(12) United States Patent
Dolan et al.

(10) Patent No.: US 12,185,960 B2
(45) Date of Patent: Jan. 7, 2025

(54) TREATMENT OF ISCHAEMIA

(71) Applicant: Versono Medical Limited, County Galway (IE)

(72) Inventors: Finbar Dolan, Galway (IE); Hugh O'Donoghue, Galway (IE)

(73) Assignee: Versono Medical Limited, County Galway (IE)

( * ) Notice: Subject to any disclaimer, the term of this patent is extended or adjusted under 35 U.S.C. 154(b) by 735 days.

(21) Appl. No.: 17/291,944

(22) PCT Filed: Nov. 6, 2019

(86) PCT No.: PCT/EP2019/080449
§ 371 (c)(1),
(2) Date: May 6, 2021

(87) PCT Pub. No.: WO2020/094747
PCT Pub. Date: May 14, 2020

(65) Prior Publication Data
US 2022/0125452 A1 Apr. 28, 2022

Related U.S. Application Data

(60) Provisional application No. 62/756,100, filed on Nov. 6, 2018.

(30) Foreign Application Priority Data

May 13, 2019 (GB) .................................... 1906743

(51) Int. Cl.
*A61B 17/22* (2006.01)
*A61B 17/00* (2006.01)
*A61B 90/00* (2016.01)

(52) U.S. Cl.
CPC ........ *A61B 17/22012* (2013.01); *A61B 90/39* (2016.02); *A61B 2017/00022* (2013.01);
(Continued)

(58) Field of Classification Search
CPC .............. A61B 17/22012; A61B 90/39; A61B 2017/00469; A61B 2017/00477;
(Continued)

(56) References Cited

U.S. PATENT DOCUMENTS 3,433,226 A 3/1969 Boyd
5,161,534 A 11/1992 Berthiaume
(Continued)

FOREIGN PATENT DOCUMENTS

JP H06-105914 A 9/1996
JP 2002-85420 A 3/2002
(Continued)

OTHER PUBLICATIONS

International Search Report of the International Searching Authority for International Patent Application No. PCT/EP2019/080449 with a mailing date of Jun. 25, 2020; 6 pages.
(Continued)

*Primary Examiner* — Jocelin C Tanner
(74) *Attorney, Agent, or Firm* — Bookoff McAndrews, PLLC

(57) ABSTRACT

An endovascular apparatus for crossing through an obstruction in a blood vessel comprises an elongate endovascular wire and a coupling. The coupling when in use transmits ultrasonic energy along the wire from an ultrasonic energy source to an active tip at a distal end of the wire. The coupling is arranged to couple the source to the wire at any of a plurality of discrete operational positions along the length of the wire for said transmission of ultrasonic energy to the active tip.

24 Claims, 25 Drawing Sheets

(52) U.S. Cl.
CPC .............. *A61B 2017/00469* (2013.01); *A61B 2017/00477* (2013.01); *A61B 2017/22018* (2013.01); *A61B 2090/3966* (2016.02)

(58) Field of Classification Search
CPC ........... A61B 2017/22014; A61B 2017/22018; A61B 2017/22038; A61B 2017/22044; A61B 2017/22094; A61B 2090/0807; A61B 2090/3966
See application file for complete search history.

(56) References Cited

U.S. PATENT DOCUMENTS

| | | | |
|---|---|---|---|
| 5,243,997 A * | 9/1993 | Uflacker | A61B 17/22012 600/585 |
| 5,248,296 A | 9/1993 | Alliger et al. | |
| 5,284,148 A | 2/1994 | Dias et al. | |
| 5,382,228 A | 1/1995 | Nita et al. | |
| 5,427,118 A | 6/1995 | Nita et al. | |
| 5,524,635 A * | 6/1996 | Uflacker | A61B 17/22012 600/585 |
| 5,542,917 A | 8/1996 | Nita et al. | |
| 5,846,218 A | 12/1998 | Brisken et al. | |
| 5,908,395 A | 6/1999 | Stalker | |
| 6,010,449 A | 1/2000 | Selmon et al. | |
| 6,577,042 B2 | 6/2003 | Lee et al. | |
| 6,695,782 B2 | 2/2004 | Ranucci et al. | |
| 2004/0024402 A1 | 2/2004 | Nita | |
| 2004/0127791 A1 | 7/2004 | Mast et al. | |
| 2004/0260180 A1 | 12/2004 | Kanai | |
| 2005/0119679 A1 | 6/2005 | Rabiner et al. | |
| 2007/0066978 A1 | 3/2007 | Schafer et al. | |
| 2007/0185501 A1 | 8/2007 | Martin et al. | |
| 2008/0294037 A1 * | 11/2008 | Richter | A61B 8/0833 604/22 |
| 2009/0292296 A1 | 11/2009 | Pansky et al. | |
| 2011/0196384 A1 | 8/2011 | Pansky | |
| 2014/0128863 A1 | 5/2014 | Song | |
| 2014/0270430 A1 | 9/2014 | Nair | |
| 2017/0215837 A1 | 8/2017 | Ramakrishna | |
| 2019/0125302 A1 | 5/2019 | Clark | |
| 2019/0262016 A1 | 8/2019 | Zheng et al. | |

FOREIGN PATENT DOCUMENTS

| | | |
|---|---|---|
| JP | 2005-507735 A | 12/2005 |
| JP | 2009-000586 A | 1/2009 |
| JP | 2015-524315 A | 8/2015 |
| WO | 9509572 A1 | 4/1995 |
| WO | 2006059966 A1 | 6/2006 |
| WO | 2006120674 A1 | 11/2006 |
| WO | 2009141810 A2 | 11/2009 |
| WO | 2014022716 A2 | 2/2014 |
| WO | 2016081025 A1 | 5/2016 |
| WO | 2016081026 A1 | 5/2016 |
| WO | 2019094028 A1 | 5/2019 |
| WO | 2019152898 A1 | 8/2019 |
| WO | 2022129623 A1 | 6/2022 |

OTHER PUBLICATIONS

Written Opinion of the International Searching Authority for International Patent Application No. PCT/EP2019/080449 with a mailing date of Jun. 25, 2020; 12 pages.

Written Opinion of the International Preliminary Examining Authority for International Patent Application No. PCT/EP2019/080449 with a mailing date of Oct. 9, 2020; 10 pages.

International Preliminary Report on Patentability of the International Preliminary Examining Authority for International Patent Application No. PCT/EP2019/080449 with a mailing date of Nov. 25, 2020; 13 pages.

* cited by examiner

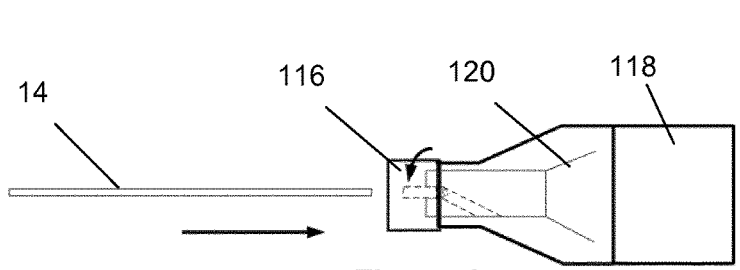
Figure 25a
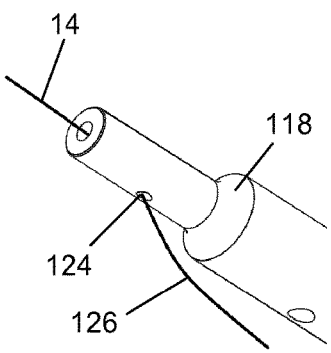
Figure 25d
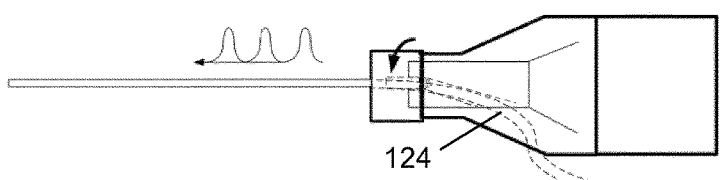
Figure 25b
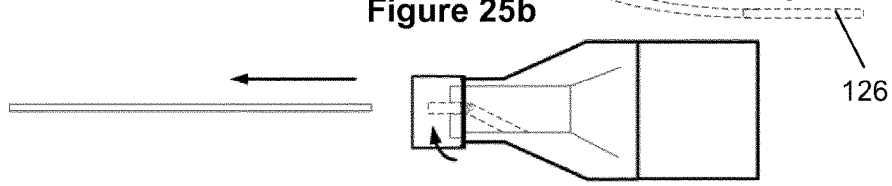
Figure 25c
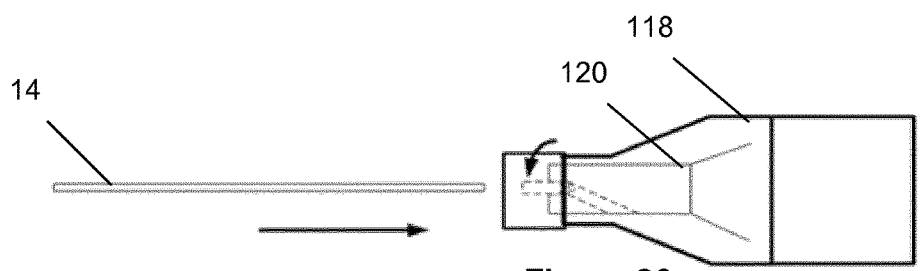
Figure 26a
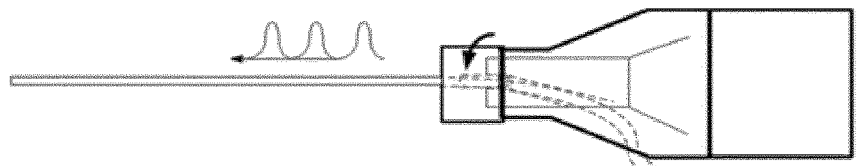
Figure 26b
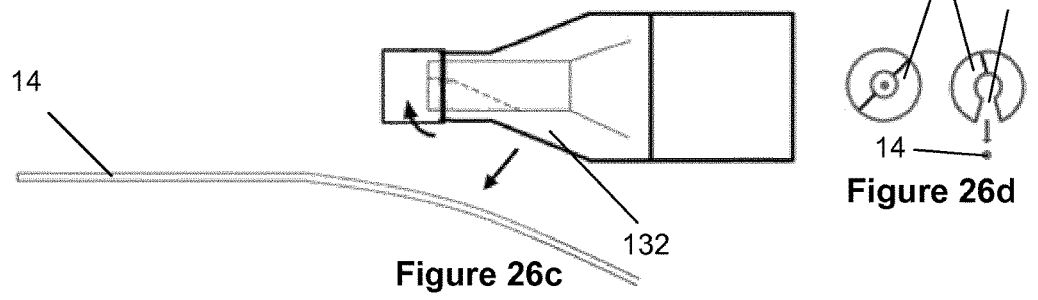
Figure 26c
Figure 26d

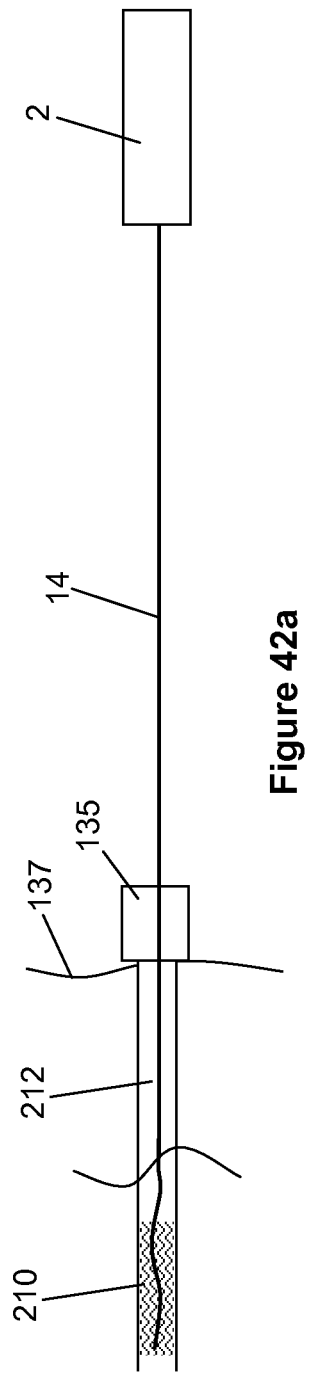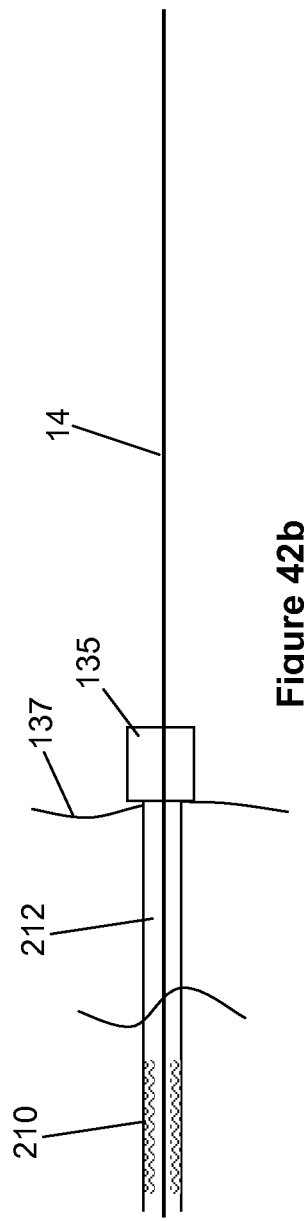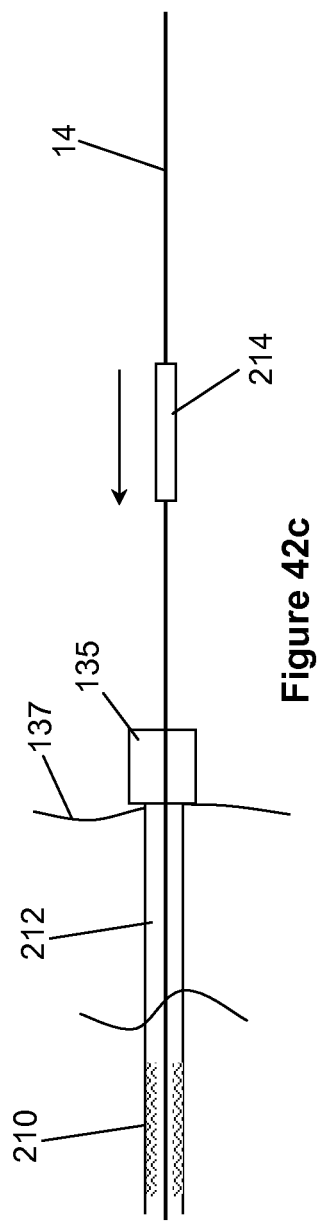

TREATMENT OF ISCHAEMIA

CROSS-REFERENCE TO RELATED APPLICATIONS

This application is the National Stage of International Patent Application No. PCT/EP2019/080449, filed Nov. 6, 2019, which claims priority to and all the advantages of U.S. Provisional Patent Application No. 62/756,100, filed on May 13, 2019, and British Patent Application No. GB 1906743.8, filed Nov. 6, 2018, the entire contents of which are hereby incorporated by reference.

BACKGROUND OF THE INVENTION

Ischaemia is an inadequate supply of blood to an organ of the body. In atherosclerotic blood vessels ischaemia occurs as a result of the blood vessels being blocked by obstructions that arise from lesions in the vessel wall, atherosclerotic plaque, or from emboli arising from other sources. Atherosclerotic plaque is composed of materials whose constitution becomes progressively stiffer over time.

By partially or fully occluding a blood vessel, a blockage restricts blood flowing to tissues, distal to the blockage, causing cell death and a rapid deterioration in the health of the tissue.

A preferential way to treat such blockages is by minimally invasive, endovascular angioplasties. In these procedures, small-diameter therapeutic devices are introduced into the vasculature and navigated to the blockage via the lumen of veins and arteries, and deployed at the site of the lesion to restore patency. These procedures to revascularise occlusions in the coronary and peripheral arteries in treating chronic atherosclerotic plaques can also be used in the treatment of acute embolic occlusions, thrombi, or occlusive blood clots.

The anatomies where these procedures are conducted include, but are not limited to, the coronary, neurovascular and the peripheral arteries that service the lower limbs. The different anatomies are associated with different lesions. Lesions found in the various peripheral vessels pose different types of challenges to those found in the coronary arteries. The iliac, femoral, popliteal and infra-popliteal arteries possess varying tortuosity, often substantially less than the coronary or neuro vasculature. However, theses arteries are susceptible to extensive calcification which poses a severe impediment to successful endovascular procedures.

In endovascular procedures, an artery is selected and recruited for use in obtaining access to the vasculature. The selection is based on the artery's ability to accommodate the passage of the intended diagnostic or therapeutic device to the target site and the extent to which it may minimise tissue and patient trauma.

In revascularising procedures for peripheral arteries, access is often made by surgical cutdown and puncture to the femoral, popliteal and pedal arteries, commonly known in medical terms as the Seldinger technique. Once the access is made, an introducer wire and an introducer sheath are inserted into the vessel and secured at the site. This sheath acts as a port for the introduction, withdrawal and exchange of devices and to minimise abrasion of the arterial tissue. Then guide catheters and guidewires are introduced into the artery, to provide further protection and to assist device navigation to the target site.

Guidewires are pushed along the lumen of the vessel, carefully to avoid causing any trauma to the vessel wall, and are navigated to the site of the obstruction. In successful procedures, the guidewires are then pushed across, or through, the obstruction and are kept in situ to act as a guide over which the diagnostic or therapeutic devices, such as balloon catheters and stents, are tracked to the site of the occlusion. Guidewires are used in other minimally-invasive procedures to introduce other devices and instruments into vessels or other cavities of the body to enable inspection, diagnosis and different types of treatment.

In the case of balloon angioplasty, after a balloon catheter is introduced over the guidewire into the vessel and navigated to the site of the occlusion, the balloon is then dilated, disrupting or squashing the occluding material and restoring blood flow. Sometimes a stent is placed over the region of the squashed lesion to act as a scaffold to maintain the vessel's patency.

Visualisation of the progression of guidewires and other diagnostic therapeutic devices being advanced through the anatomy is typically done by X-ray or duplex ultrasound. MRI is increasingly popular in other anatomies.

The other medical procedures that use guidewires referred to in the above include gastrointestinal, urological and gynaecological procedures, all of which require a passageway to be formed through a blockage to facilitate the passage of larger and often more cumbersome devices to the site of lesions or other tissues targeted distal to the lesions in the body.

Guidewires are key to therapeutic intervention and are manufactured from different materials, most typically stainless steels and NiTi (nitinol), with many different designs. Their manufacture involves the modification of the microstructural morphology of the material, for example by cold-working the material while forming it into a wire and then machining the wire to different dimensional designs to effect a desirable performance. As an example, specific tapers may be machined over the length of a wire to produce differential degrees of flexibility along the length of the wire. So, at its distal end, the wire will have sufficient flexibility to conform to the shape of the vessel, and strength to transmit force to the tip ('tip strength') or force to cross through the lesion.

The construction of these devices usually includes a thin coil that may extend over the entire length of the wire or discrete sections, most typically the distal section. These coils assist in the transmission of force over tapered sections and increase the force that can be transmitted through the entire length of the wire. They also allow the wire to conform easily to the shape of vessels and to track through the tortuous anatomies that can be encountered, especially in coronary and neurovascular anatomies.

The wires are made available in a range of outer diameters associated with the anatomies that they are treating. Wires of the order of 0.010" (about 0.25 mm) in diameter are commonly used in neuro-vasculatures, whereas wires with an outside diameter of 0.014" to 0.018" (about 0.36 mm to about 0.46 mm) are typically used in coronary applications. These 0.014" and 0.018" (about 0.36 mm and about 0.46 mm) wires are also used in many peripheral vasculatures, typically in infra-popliteal pedal and tibial anatomies. In accessing and treating diseased larger-diameter and straighter vessels such as the iliac, aortic and thoracic vessels, wires with a typical outside diameter of 0.035" (about 0.89 mm) may be used. Wires with an outside diameter of 0.016" (about 0.4 mm) and 0.018" (about 0.46 mm) are common in accessing femoral, popliteal and sub-popliteal vessels.

The length of wires used in endovascular procedures also varies depending on the distance over which they are considered likely to operate. As an example, wires typically of 750 mm up to 900 mm in length are used in many peripheral applications where they may be introduced in femoral or popliteal anatomies, or need to track to and through blockages in ipsilateral iliac femoral popliteal and infra popliteal arteries. Wires that are used in contra-lateral and coronary applications tend to be of the order of 1200 mm, 1500 mm or 1700 mm in length. Indeed, wires that may be tracked contra-laterally may be longer, perhaps of the order of 2000 mm to 2250 mm or 2500 mm in length.

These conventional endovascular wires are passive, in the sense that they do not transmit any energy other than that applied by the clinician. They are of varied constructions and designs to facilitate access and crossing of lesions in different anatomies and for different devices. However, in very many instances the occlusions are too challenging for conventional wires to cross through.

In the case of peripheral arteries these blockages are often too severely diseased and composed of materials too resistant to allow the passage of the wire and in these instances the endovascular procedure either takes substantially more time to do, or often it requires many more devices to cross the lesion or quite often it is simply abandoned.

In over 50% of peripheral artery cases, particularly in the popliteal, tibial and peroneal arteries, the vessels are totally occluded by lesions; in approximately 30% of cases the target lesions are severely calcified. These calcified lesions are in effect composed of rigid inelastic segments that typically extend to a length of 3 cm to 5 cm within even longer extensive diffuse lesions that are, on average, of the order of 20 cm in length. Selecting a treatment for these lesions requires insight as to their length and composition that is not readily available from conventional imaging.

If a guidewire is unable to cross a lesion in a vessel, it significantly impacts on the likely success of the procedure. Failure of the guidewire to cross a lesion in a vessel prevents preferred follow-on procedures such as balloon angioplasty and stenting and limits the ability to treat the patient.

Occlusions in the distal, infra-popliteal vessels or the anterior, posterior tibial and peroneal arteries result in an ischaemic response to wounds and trauma, leading to refractory ulceration of wounds and cuts and other insults to tissues. This anticipated response makes surgical intervention less attractive, promoting the need for an endovascular solution for chronic total occlusions (CTOs).

The result of conventional wire designs often being unable to cross through intractable lesions has led to the development over the past two decades of advanced minimally-invasive endovascular surgical techniques, which employ conventional guidewires and balloons. The procedures are technically challenging, requiring significant skills and training and specialist devices that have been created to enable them to be done more efficiently. Techniques such as the sub-intima and retrograde approaches have evolved and re-entry devices have emerged to assist the procedure.

Sub-intima techniques bypass the lesion through the formation of a new pathway by tunnelling along the tunica intima, around the media over the length of the lesion and re-enter the vessel distally. These pathways are established by balloon dilation and stenting to sustain their patency. Re-entry devices have been developed to facilitate these procedures.

Retrograde techniques take advantage of the softer distal cap of occlusions, which is easier to cross than the calcified proximal cap encountered in the antegrade (femoral) approach. In these retrograde techniques, access is obtained through vessels distal to the lesion in the foot or ankle in the case of peripheral disease; or through collateral (typically septal) vessels in coronary anatomy. These procedures are more complex; they require greater skill and take much longer to do.

In peripheral infra-iliac procedures, time is spent in attempting the conventional (antegrade) approach and escalating through wires in further antegrade attempts before escalating to retrograde approaches to cross the lesion.

In healthcare systems, where resources are finite, an increasing demand makes the adoption of these life- and limb-saving endovascular techniques problematic for the clinical community. They arguably offer the best patient outcomes, consume less hospital and community care resources and provide a better fiscal outcome for the healthcare system. However widespread awareness of these outcomes, finite hospital and clinical resources and the significant level of clinical training and practice required for current techniques limit adoption.

Conventional endovascular guidewires are passive mechanical devices with no active components. They are operated by their proximal end being pushed, pulled and torqued to navigate to the blockage site and are then pushed through or around the blockage. Their designs balance surface characteristics, stiffness and flexibility to optimise the way in which they navigate and act in delivering a therapy. These passive wires do not work as guidewires are intended to, or they are limited when trying to cross near- or totally-occluded blockages that may also be significantly calcified.

BRIEF DESCRIPTION OF PRIOR ART

The broad approach of using ultrasonic vibrations transmitted via small-diameter catheters and assemblies has been established in both expired and recent prior art, as exemplified by U.S. Pat. No. 3,433,226. U.S. Pat. No. 5,971,949 describes the transmission of ultrasonic energy via waveguides of different configurations and tip geometries. U.S. Pat. No. 5,427,118 describes an ultrasonic guidewire system but does not discuss in detail proximal geometries of the wire or how it facilitates follow-on devices via over-the-wire methods.

Many current single-transducer systems are not ultrasonically-activated guidewires but are instead, ultrasonically-activated catheters that contain wire members to agitate and ablate material. U.S. Pat. Nos. 6,855,123 and 4,979,939 describe such systems. These catheters themselves require a separate passive guidewire to help them navigate and, as such, are tools to facilitate a separate guidewire crossing a blockage. U.S. Pat. No. 9,629,643 shows a system with a range of distal tip configurations but all requiring a separate guidewire for access.

These devices are directed towards delivering an alternative method of revascularisation and are described as atherectomy devices. They do not identify crossing through the lesion to facilitate the delivery of devices to effect revascularisation by conventional PTA and PTCA therapeutic devices.

In the art, these ultrasonic devices and recanalisation wire devices are associated with claims that they enhance the clinical atherectomy procedure. They enhance revascularisation and provide for, or effect, an atherectomy by debulking the lesion by removing the plaque that forms the lesion.

Many prior art disclosures cite the reduced likelihood of vessel dissection, as a consequence of the operation of such devices which is atraumatic to soft compliant tissues. Some ease the movement of the wire through the vasculature without dependence on hydrophobic or hydrophilic coatings.

There is also repeated mention within the art of how the vibration of ultrasonic intravascular devices can reduce the likelihood of vasospasm, an adverse event that can arise in the course of any angioplasty procedure using conventional devices. This therapeutic benefit is considered to arise from the effect of vibrations of the wire massaging the tissue, see U.S. Pat. No. 5,324,255.

Early investigators of these revascularisation devices reported in the open literature how their efficacy was influenced by contact with tissue, and they explained how they increased power in the system to overcome the losses by manually adjusting the voltage in stepped increases to overcome the losses. This illustrates the need to impart some means of overcoming the impact of losses, such as varying voltage to increase amplitude, or varying frequency.

In later and current designs, ultrasonic generator systems have become large units, scaled to generate and control the pulsed wave. Whilst electronics today would make it possible to package such systems in smaller forms, the cost of miniaturisation militates against this. Also, practical utility considerations mean that known systems commonly comprise separate elements. For example, many systems are designed with the signal generator housed in a separate unit from a transducers, some being mounted on large trolley units that take up significant space in the clinical environment. U.S. Pat. No. 6,450,975, US 2008/0228111 and U.S. Pat. No. 9,282,984 all describe such systems.

In the prior art, many systems describe semi-automated control of amplitude through a feedback loop monitoring current. This provides a means, by modulating voltage, to achieve a maximum tip displacement through the passage of the device through the vasculature and in tunnelling through the lesion. These systems do not relate this modulation directly to tip displacement and tunnelling effects or to the composition or character of the lesion.

U.S. Pat. No. 6,577,042 to Angiosonic describes the modulation of output amplitude through current in an algorithm that interrogates the transducer current over a small range of frequencies. This maintains power at a constant level and also monitors the current and voltage over a small range of frequencies to detect the failure of the sonotrode, the activated member, and to confirm the optimised output frequency.

WO 2018/002887 to Soundbite describes a different approach in which multiple transducers or wave focussing are used to generate a concentrated wave profile. Again this results in the requirement for a large physical unit. The unit constructs the output ultrasound wave through the orchestration of soundwaves generated by the transducers in the device, by taking at least two different component waves and combining them in the waveguide to form the desired output wave. These methods all require substantive data acquisition and computer systems to effect the solution.

The method by which mechanical waveguides or transmission members are coupled to the horn is critical and many connection methods are disclosed. U.S. Pat. No. 4,572,184 discloses a method that uses a screw connector with the wire retained in the screw. In addition to the internal connection mechanism there are a number of patents, such as U.S. Pat. Nos. 6,508,781, 5,971,949, 5,417,672 and 9,433,433, associated with design features to allow the user to interact with these mechanisms.

Constraint in the lateral direction is also cited to optimise the manner in which the wire will migrate through the vessel. The literature also cites the provision of strain relief at the transmission juncture.

The nature of the wire has been addressed in respect to its form, or shape, with solid wires such as disclosed in U.S. Pat. No. 6,589,253 most common although proposals for hollow constructions as in U.S. Pat. No. 4,538,622 also exist. Modifying the wire through tapering to drive distal tip displacement is cited, as well as to optimise resonance along the length of the wire. The composition of the material is also critical in terms of type and combination and composite material constructions, for example as disclosed in U.S. Pat. Nos. 8,500,658 and 5,397,301 respectively.

Ultrasonically-activated catheter and wire systems have been considered in the past as a method of atherectomy and to prepare vessels for angioplasty treatment. Some products have been made available commercially in the past, some remain available on the market and some new systems have come to market recently. These various types of catheter are referenced below.

These catheter and wire systems often include a) an ultrasonic generator that converts mains electricity into an ultrasonic waveform, defined by its voltage amplitude and frequency; b) an ultrasonic transducer and often an amplifying horn that converts the electrical energy into high-frequency mechanical vibrations, defined by frequency and amplitude of vibration; and c) a small-diameter waveguide coupled to the horn that transmits the mechanical vibrations to the distal tip of the wire. This results in the distal tip of the wire vibrating at a desired amplitude and frequency with the goal of ablating material and ultimately facilitating the revascularisation or recanalisation of vessels and anatomical structures throughout the body.

Tissue and material in the vicinity of the distal tip are affected by a combination of the ultrasonic movement of the tip and its direct mechanical abrasion, ablation and cavitation from the pressure wave components and acoustic streaming that removes ablated material from the zone around the tip.

BRIEF SUMMARY OF THE INVENTION

The present invention is a disruptive advance over conventional endovascular guidewire designs and existing activated guidewire and catheter systems, where mechanical vibrations are transmitted via the wires to the distal tip.

Aspects of the inventive concept are expressed in the appended claims.

Disclosed is an ultrasonic system that induces vibrations in customised endovascular surgical wire devices, interrogates and applies artificial intelligence and/or smart electronics to feedback in the system to use in optimising the performance of the device in navigating to and crossing through and characterising endovascular occlusions.

The invention provides a device whose purpose is to rapidly penetrate and traverse any occlusion of any composition in any artery or other vessel. The device could be used in a stand-alone procedure to effect revascularisation and to restore blood flow in pedal applications or other instances. However, the device is most advantageously used to facilitate follow-on transportation of endovascular diagnostic and therapeutic devices to effect and assist in the revascularisation of the blood vessel.

The objectives of the ultrasonically-active guidewire device are 1) to cross through complex and calcified vessel occlusions, either as a standalone procedure, or as an activated or passive guidewire and 2) to provide a conduit to enable the passage of ancillary devices to effect revascularization and scaffolding of the vessels.

In the literature, in patents and in products brought to market, the concepts for a wire or an ultrasonically activated system have all located and clamped the proximal end of the device.

Embodiments of the invention provide for transmission or activation to be made at intervals anywhere along the length of the wire. This allows the activation device to be moved along the length of the wire or to be left at a specific location, e.g. close to the activation port and the wire moved in and out of the device to prepare for crossing a therapeutic device.

In one sense, the invention resides in a system that comprises three interlinked components, namely: a) a compact housing and components acting as an ultrasonic source and connector; b) an active crossing wire assembly for entering an anatomical system and transmitting the energy to an active distal tip; and c) a signal acquisition, processing and communication chipset. The compact housing unit has an ultrasonic generator; an ultrasonic transducer, a horn and a control unit, that are all co-housed in a portable compact housing unit designed to connect through a coupling unit that excites the endovascular crossing wire and monitors and modulates the excitement of the system in order to effect the crossing and characterisation of endovascular occlusions. The on-board signal acquisition and processing chipset can acquire and control the excitation of the signal generator and provide for the communication of outputs from the system to its users and/or external data acquisition systems.

The invention resides in a device that activates the endovascular crossing wire ultrasonically, advantageously along its whole length. Upon being decoupled from the activating unit via a detachment means of the invention, the crossing wire has a nominal outside diameter that can enable the wire to act as a primary crossing device.

The activating unit may be coupled to and decoupled from the wire and coupled at intervals along the length of the wire. When decoupled, the activating unit also facilitates the passage of therapeutic devices, such as atherectomy vessel preparation devices, angioplasty catheters and stents, over the wire to the site of the occlusion.

A controller may monitor measurements of frequency and amplitude of current and voltage and of incident, reflected and standing waveforms and may thereby estimate distal tip displacement. Modulation of these variables may be monitored as the wire transits through the anatomy and crosses through different types of occlusions, including calcified chronic total occlusions. Determination of calcific versus non-calcific lesions and of the duration or length of a calcified segment is key to some aspects of the invention.

The signal used to drive the ultrasonic generator may be pulsed or varied to reduce heating and to optimise analysis and matching of offsets at the resonant frequency. A pulsed modulation of voltage, over a small frequency range, may activate the crossing wire. A digital signal processor unit may interrogate the measurements made, provide feedback and interpret and compare the relative contributions of losses from anatomical tortuosity in navigating to the site versus those arising from passage through the occlusion.

A specific algorithm, for each standard wire type, may be employed to estimate the diameter mapped out by the deflection of the distal tip when excited at different levels of frequency and power and device configuration in the conditions pertaining to the procedure. The algorithm may estimate the diameter along the length of a tunnelled section through the occlusion.

The system of the invention may process data obtained from measurements that are indicative of the ultrasonic waveform as it is generated, as it passes through the transmission member and as transformations of the resonant vibrations occur, as the reflected waveform is attenuated by a transmission member, while passing through the vasculature and through occlusions. This data is processed or operated upon by on-board algorithms to perform operations to transform the raw data into procedurally-relevant outputs.

Where the modulation of transmitted signals is monitored and analysed, the system of the invention can adjust, possibly automatically, for energy losses in the system through voltage control to increase power in the system and compensate for energy losses encountered in the wire as it is passes through the vasculature to the occlusion. The system can distinguish these losses from the additional losses as the wire passes through an occlusion and can compensate for the latter losses to sustain displacement at the distal tip.

The measured parameters and variables may be operated on numerically to determine the rate of change of those measurements relative to each other and other parameters. The system of the invention can numerically compare and interpret the difference between these calculated values from the active system and a prescribed set of values in order to characterise the nature of a material occluding the vessel. Optionally, energy can be controlled manually by an over-riding controller that enables a user to increase the power in the system and therefore the level of energy to drive the waveguide. A means of providing a manual pulsed override through the adjustment of current or voltage can be used to immediately, or pre-emptively, address sudden losses in the system due to unexpected events or interference to the wire.

The outputs can be presented visually on a small display or via tactile or audio hardware, such as a haptic interface, located onboard a device that is accessible and visible to the user.

Optionally, the active crossing wire assembly can be utilised in a passive mode with no ultrasonic activation, or the wire can be mechanically coupled to the ultrasonic transducer and acoustic horn in the housing unit to transmit ultrasonic vibrations, and then the wire can be detached from the housing unit to return it to a configuration for follow-on procedures.

The active wire assembly can be connected by a means for connecting the active wire assembly to the acoustic horn and compact housing unit in a manner that allows for efficient transmission of the ultrasonic vibrations to the wire assembly. A geometrically shaped proximal tip may be optimised to easily locate, load and interference fit into a coupling connector to facilitate rapid loading and unloading and faithful transmission of energy through the wire.

The proximal end of the wire may be machined to a form that allows it to locate into and engage in direct contact with the acoustic horn. Once the wire is located in this position, a secondary mechanism may clamp or lock into position mating with the circumferential surfaces of a lock unit, whereupon the wire remains in place until the mechanism is released.

A custom active crossing wire assembly can be presented to the system with an integrated locating boss that allows the part to locate in or out of the coupling for the procedure. A means may be provided for rapidly decoupling an ultrasonically-activated endovascular wire from the acoustic horn by means of a mechanism that cuts the wire in a precise controlled manner to allow the remainder of the device be used as a delivery wire for follow-on procedures. A boss may perform functions of either, or both, coupling and cutting or fracturing of the wire.

A custom active wire assembly may have features to optimise radiopacity under high frequency deflection, placed at regular intervals along its length and that are visible under duplex imaging. Such features may be machined and/or may comprise marker bands, for example of gold or platinum. Ultrasound as well as X-ray can be used to estimate the length of the occlusion during the procedure.

A distal tip edge of the crossing wire may be rounded and polished to limit the likelihood of trauma to tissue and may be manufactured from a scratch-resistant material that is optimised to cross through the lesion.

A custom crossing wire of the invention may have a formable or shapeable distal tip for steering and radiopacity for visibility to provide for more efficient tracking to and through target lesions and to facilitate access to side branches.

The crossing wire is constructed from a resilient fracture-resistant material such as low inclusion density nitinol wires of ASTM Type I to Type IV, with the selection based on optimised properties for different diameters and target anatomies.

The crossing wire may have lubricious hydrophilic and hydrophobic coatings and/or a low-friction jacket to further minimise adverse effects from fretting and to minimise the potential for coagulation.

A controller may process all measurements of the transduced emitted wave and received waveforms. A user interface may communicate the performance and progress of the device in advancing through any blockage and provide feedback on the characterisation of the composition and length of the lesion via visual, audio or tactile means such as haptics.

The system of the invention can enable communication of data between the device and another device or wireless or cloud service for analysis and storage.

An ancillary device attached to a Luer device through which the wire passes may provide telemetry relating to the movement of the wire through the vessel.

An automated drive may be used to carefully control the speed of insertion and withdrawal of the wire into the vasculature to provide for more precise feedback on the composition of the plaque through the length of the lesion. This provides a means to effect more sophisticated characterisation of the lesion and the endovascular environment.

The acoustic horn and the transducer assembly may have a hollow port through the full length of the assembly, with an internal wire connect/disconnect mechanism or locking collet.

The system of the invention may comprise three interlinked components where the components of the ultrasonic system are disaggregated. For example, the generator may be separate from the compact unit.

The wire may be fixed in a crimped sleeve that captures the wire over the length of the sleeve. The sleeve may be cylindrical or may preferably be of polygonal cross section, for example a hexagonal or octagonal pattern, that collapses onto the wire in a uniform manner. The sleeve, or other coupling structures such as collets, may for example be made from stainless steel or from aluminium.

The crimped section may be applied under a controlled force and the wall thickness of the collapsed sleeve ensures that a uniform load is applied to the wire. Conveniently, the proximal end of the crimped sleeve may be threaded to screw into the transducer head. Alternatively, the wire may be fixed in a crimped setscrew that captures the wire at the proximal length.

Construction

In preferred embodiments, the system of the invention comprises:
a) a signal power generator;
b) an ultrasonic transducer;
c) an optional acoustic horn;
d) a transmitting waveguide or crossing wire, which can transmit high-frequency ultrasonic vibrations from the proximal end to its distal tip to ablate through non-compliant materials that are blocking the artery and is of a dimension to facilitate standard diagnostic and therapeutic devices;
e) a coupling, an attachment mechanism that couples the transmission wire to the acoustic horn, or directly to the transducer, that minimises losses and enables the faithful transmission of high-frequency mechanical vibration;
f) a means of decoupling or detaching the transmission member from the acoustic horn or the transducer, which may, or may not, utilise the attachment method; and
g) a programmable circuit system that comprises an integrated, or on-board, programmable digital signal processing chipset, to process the monitored, transmitted and received/incoming signals through algorithms that interrogate the response, compare the ultrasonic feedback and effect on the resonant frequency standing wave, estimate the size of the opening tunnelled through the lesion by the activated tip and modulate the power in the system via the amplitude of voltage and system frequency.

For the purposes of the following description, the system can be considered to be composed of four main sub-assemblies and sub-systems:
1) A compact housing unit, which may or may not be handheld, to control the operation of the medical device and which houses all or some of the following parts, namely, the signal generator, the ultrasonic transducer, the acoustic horn (although the horn could be part of the transducer assembly or may be omitted) and interface coupling components, as well as data acquisition, processing and system control.

Different embodiments of the device system are envisioned. In one embodiment, all of the components are aggregated in a single unit. In another embodiment, the components are disaggregated, with the generator housed separately. In another embodiment, the transducer horn is separated. In another embodiment, the coupling connects directly to a transducer stack.
2) A coupling and detachment module that allows the crossing wire to be connected to the ultrasonic transducer and/or horn assembly.
3) A set, variety or series of interchangeable flexible transmission member assemblies or crossing guidewires for the minimally invasive percutaneous surgical recanalisation of blocked or partially blocked anatomical passageways.
4) An integrated signal processing circuit board, for data acquisition and processing and controlled activation of the system. This processing board is capable of analog and/or digital signal analysis and power control of the device as well as incorporating communications modules in some embodiments. This enables wired and wireless connection of the device and its data to wider data networks and the internet, and facilitates the development of more intelligent algorithms to manage the system.

Operation

Overall, the system operates as follows: a) the signal generator provides electrical energy to the transducer; b) the piezoelectric ultrasonic transducer converts that electrical energy into mechanical vibrations; c) these mechanical vibrations may be further amplified by an acoustic horn; d) the customised transmission member is coupled to the acoustic horn or to the transducer via a customised coupling method; e) the ultrasonic vibrations are transmitted via the transmission member; f) the distal tip of the transmission member vibrates at a prescribed frequency and amplitude with the capability of beneficially disrupting the diseased tissue or other material; and g) the digital signal processing and control circuitry allows semi-autonomous gross characterisation of the lesion, power control and the estimated size of opening in the system.

When the ultrasonic system is activated, the emitted waves travel along the wire to its distal tip where they are reflected. Reverberations created in the wire at different transitionary points establish a series of secondary and tertiary reflections. These waves are characteristic of different wire designs and features and they can be optimised to heighten the difference in the features of their signals. These reflections are determined to be composed of a specific pattern of response in the waveform at any time for a given input and their variation is associated with perturbations or differences in the ambient environment.

The amplitude of displacement along the wire, at specific frequencies, varies through the course of a procedure as a result of damping from contact with surrounding tissues, either during navigation to the site of a lesion or in contact with diseased, non-compliant or calcified tissues in a lesion. Compensation for these losses is made by, for example, increasing the voltage or the current in the generator and then in the transducer. This is used to drive the amplification and/or the attenuation of the primary ultrasonic energy. The reverberations in the system are affected similarly to the primary losses, in characteristic ways, that allows their use in crossing and excavating a lesion and in characterising the source and the nature of what is causing damping.

Control

To achieve a constant vibration amplitude, the ultrasonic transducer is controlled by a suitable feedback controller. In the case of the ultrasonic waveform, phase feedback control and comparison can be made by an electrical equivalent model, e.g. the Butterworth—van Dyke model.

The ultrasonic transducer can be controlled by the frequency and the amplitude of the excitation voltage. The manner in which changing the frequency influences the phase between the voltage and the current is employed in an embodiment of the invention.

Here, the amplitude of the excitation voltage controls the current and is proportional to the vibration amplitude in resonance. This allows control algorithms to employ only phase and amplitude to drive frequency.

In a preferred embodiment, the approach is to drive the system using the resonance frequency as the operating point of control, in conjunction with an amplitude feedback controller, managing this operation through the use of customised programmed control algorithms that are unique for each wire type.

The advantages of a resonant-driven, low damped system are the low voltages necessary and the high values of effective power. This technique is novel in the context of an active guidewire system. It also offers additional advantages in controlling the response of nitinol wire systems to ultrasonic activation.

Preferably, the wire is activated at a frequency of 40 kHz for the purpose of advancing to a lesion and also crossing the lesion. The amplitude of the signal is determined by the degree to which it may find resonance in the system due to perturbations in contact in a tortuous pathway or in contact with a lesion forming a total occlusion or a thrombus or some embolic material. An activation frequency of 40 kHz has been found to be effective at producing a crossing/excavation action at and around the distal end portion of the wire and to assist in driving the wire to and through the lesion.

An activation frequency of 40 kHz enables the transmission of ultrasound energy over a functional working length of 750 mm or less to 2 m or more, for example 1.5 m, for distal tip activation with sufficient strength to achieve resonance over a range of harmonics and with sufficient energy to effect crossing as well as excavation.

Basing the system on an activation frequency of 40 kHz also enables components to be sufficiently compact that they may be contained in a handset of compact size and convenient form. Using a 20 kHz system instead, for example, would require the transducer to be multiplied in mass and size, in both length and diameter.

Transducers can be designed to have a desirable resonant frequency based on their material properties, geometry and pre-stressing. Broadly speaking, the higher the resonant frequency of the transducer, the smaller its size and overall dimensions. For example, a transducer and horn configuration operating at a frequency of 40 kHz can be made to be hand-held and compact. It is this that allows the production of a hand-held transducer that can easily be used with a wire. In particular, a small transducer can easily be moved along the wire by a single operator and can easily be stowed or fixed at a particular location along the wire.

The concept of such a system has been established to effect an atherectomy and remove the lesion as an obstruction. One function of the device described is therefore to achieve this. However, the product platform proposes another function, namely to act as a guidewire to deliver a therapy or therapeutic device to the site of the lesion. The wire crosses through lesions of any composition by using ultrasonics to transform the guidewire temporarily into an activated wire, which allows the wire to cross lesions that are otherwise uncrossable except through circuitous techniques.

Temperature effects in nitinol and changing load conditions during the process due to the interaction with the surrounding tissues that can potentially result in a change of the resonance frequency and vibration amplitude can be compensated for, within a range, for a given transducer.

Thus, it is disclosed that in an embodiment of the device, in the use of voltage and current, use will be made of control and analysis through the resonant frequency to monitor the differential changes, over time and length and that this interrogation and compensation will be used to characterise the nature of the endovascular anatomy.

Algorithms

The comparison and analysis of and between the primary emitted and the tertiary feedback responses in the wire considers variations in characteristic losses, typical of the engagement of the active member with different, healthy and diseased tissue types. The analysis differentiates between losses in the vessel and losses associated with lesions and between lesions of different composition, especially between calcified and non-calcified lesions.

The resistance load encountered and recorded by the system varies as the active member passes though different anatomies. Analog signals are interrogated by on-board digital signal processing (DSP) and conditioned and the parametric output is processed by algorithms to characterise response and to define feedback and effect control.

The characteristic response to differential changes occurring in different media and in the passage or navigation of the endovascular wire through different anatomies is used to create distinct algorithms that are used to: 1) determine the source of and to compensate for losses in the system; 2) assess the tone of arterial vessels; and 3) determine the composition detail of a lesion. These algorithms provide an automated level of compensation to the tip of the wire as it comes into contact with compliant, non-compliant and calcific material and in the latter to amplify the energy in the system to increase cavitation and the formation of the de novo lumen.

Algorithms may be customised to the wire type. The range and the rate of change and the differential order of the change, filtered by the signal processing circuit, may be used by the algorithm to characterise the nature of the material through which the wire passes. This may then be communicated to the physician as the procedure is being undertaken to assist in defining therapy.

Improvement in Performance

Advantageously, the algorithms may be trained by bench ex vivo and in vivo data. The latter is enabled by an embodiment of the device with a communications mode that provides for the transportation of data to and from the device. Thus the quality of the operation of and the interpretation by the device can be improved over time by the interpolation of more data sets from additional procedures that builds upon the use experience and evidence, which can be released into iterative generations of control algorithms for the product.

This on-board, local and cloud-based refinement of algorithms improves the design and operational interface of the device. It also provides more detailed feedback to the physicians using the device and facilitates customisation of operation of the device to suit different wire geometries and anatomies.

Coupling and Configuration

The ultrasonic generator, the main housing, circuitry and coupling components remain external of the patient. Most of the length of the transmission member and components of any peripheral catheter are the only parts of the system that need to enter the patient's body. The proximal section of the transmission member and any peripheral catheter components remain external to facilitate coupling to the main unit and procedural requirements of steering and control.

A first concept of the invention resides in a detachable active crossing guidewire. In this way, an active crossing wire can serve as a guidewire for follow-on therapies post crossing. This involves a method of operation in which the crossing wire can be used in passive and active configurations. The crossing wire can be connected to and detached from the transducer housing at the point of care.

In the preferred method of operation, an endovascular crossing wire can initially be used in an anatomical passageway in a passive mode with no ultrasonic vibrations. While the wire remains in the anatomical passageway, the proximal end of the crossing wire can then be attached to the acoustic horn/transducer assembly located in the housing, as required, to energise or transmit ultrasonic vibrations via the wire acting as a transmission member, resulting in vibrations at the distal tip to effect crossing of the lesion.

Following ultrasonic activation, the crossing wire can then be detached or decoupled from the acoustic horn located in the housing to return to a passive wire configuration to facilitate further follow-on devices or therapies, if required.

The ultrasonic transducer, horn, coupling means, signal generator, power and control circuitry may all be located in the same hand-portable, lightweight compact housing unit. In another embodiment, the signal generator is separate and is joined to the compact housing unit containing the transducer and horn, via a connector cable. In another embodiment the entire system may be designed as a single-use device. In another embodiment the ultrasonic transducer, horn, coupling means, generator and control circuitry may all be located in the same portable compact housing unit and connected to power via a cable.

Disclosed is a customised transmission member or wire, which will act as the endovascular crossing guidewire, designed and customised to efficiently transmit vibrational energy over its length and to effect a controlled ablation at its distal tip.

Also disclosed are a number of methods of mechanically coupling the transmission members to the acoustic horn or the transducer located in the housing. The coupling arrangement may also, used in reverse, act as a decoupling arrangement.

Also disclosed, the system may include a separate decoupling component to quickly detach the transmission member proximally from the overall system, facilitating its use as a follow up-guidewire or positioning device.

The coupling and decoupling mechanisms may be housed in either a) the main housing where the transducer and horn are housed or b) as part of the proximal housing which is part of the transmission member assembly.

In another embodiment the transmission members are pre-coupled to the acoustic horn located in the housing at the manufacturing stage.

The design of the coupling is optimised in order to effect efficient transmission and to limit undesirable strain and acoustic transmission losses.

The coupling method is designed for easy user interaction, coupling and visual/tactile feedback of coupling status.

In one embodiment the transmission member is part of a customised wire assembly with a proximal housing which includes the coupling and decoupling arrangements and wire supports to minimise losses in the delivery of energy through the proximal section of the transmission member. This custom assembly and proximal wire section allow for better guidewire control and access during passive crossing. The design of the coupling mechanism is optimised for the transmission of acoustic ultrasonic energy from the transducer and/or the acoustic horn. The manner in which the wire is engaged is important to effect the desired transmission of actuating forces over the length of the waveguide to the distal tip.

The system delivers a controlled level of energy to the transmission member through the custom coupling to effect minimum losses and can guide the initial deformation of the transmission member to minimise losses and unwanted loading of the transmission member.

The design of the transmission member or waveguide wire is optimised to control the transmission of the wave pattern through different anatomies to the distal tip and through different materials. The morphology of the materials used is important and whilst they can, at a macroscopic level, present as an isotropic material morphology that is highly resilient, they can have anisotropic micro-morphological features that can either delay the onset of a starter crack or inhibit the progression of a crack.

In order to deliver disruptive vibrations to the location of a lesion, the invention contemplates custom-built crossing wires to resonate at the driving frequency of the system. This is achieved through knowledge of material properties, including speed of sound and density, in addition to resonant characteristics of slender rods and numerical modelling.

The crossing wire may be manufactured from a single piece of drawn wire of may be constructed by joining sections together end-to end.

Proximal features may be included to enhance coupling of the wire to an ultrasonic driving unit and to reduce the risk of fatigue failure. Conversely, distal features can be included to enhance performance in navigation and crossing, including control and steerability of the wire optimised for tracking through anatomies and also to increase the opening profile achieved. Additionally, marker bands may be included to provide visibility under fluoroscopy or x-ray. Radio opaque markers may, for example, indicate the working length and the crossing tip of the wire.

More generally, the invention allows for the introduction of specific features that are machined into the wire at the proximal and the distal ends and over its length to enhance the ability of the wire to cross through a lesion, to strengthen the wire, to enable greater control over the wire, and to enable coupling of the wire and efficient transmission of energy through the wire. The composition of the designs varies with materials used and the intended use.

The geometry of the wire as well as the materials used are optimised for different application applications. The wires are machined to minimise defects and to optimise the transmission through tightly-controlled tapers and keying splines over the length and through sections of the length of the material.

The materials used in the exemplary embodiments are nickel titanium (nitinol) alloys. Specifically, in the case of nitinol alloys, tight control is exercised over the size and population of inclusions in order to limit the likelihood of fracture.

The design of the distal tip and any geometrical features utilise modern manufacturing methods and have geometries optimised to enable different effects. As non-limiting examples, these effects include: limiting trauma to tissue; accelerating passage of the waveguide through different anatomies; and limiting unnecessary lateral deflection through different lesions of different types. The lesions can be of different length, diameter or composition or be thrombotic or calcific in origin. The distal tip is also optimised in order to open out or increase the diameter of the passage to provide for follow-on therapeutic devices, if required.

The invention may include a novel semi-automated control system that can control or modulate the signal from the generator applied to the transducer and horn and hence to the crossing wire. Control may be based on feedback from the wire-tissue interaction in order to control the signal being transmitted to adjust for losses due to damping or increased resistance or for modulating applied force.

Embodiments of the system comprise visual and haptic feedback indicators that can offer visual, audio and/or tactile feedback to the user regarding the status of the device and the nature of the tissue being ablated. Such feedback may also indicate the level of force that can be applied to effect ablation and disruption of the tissue and progression of the crossing wire.

The system may contain a means to provide a manual override to assist the control of the amplitude of vibration delivered to the distal tip. This allows the system to be controlled by the user operating the device in the course of the procedure, through controllers and user input mechanisms located on the generator and transmission unit, or to be autonomously controlled.

The transmission coupling and controller unit may contain sensory feedback systems and haptics that allow the user to sense how well the wire is crossing a lesion.

In the device described herein the frequency at which the converter transduces a mechanical signal is at a set short-range frequency sweep, over a short range of frequencies, to accommodate the losses from interaction and impingement by different forces over the length of the wire. The speed of the microprocessor allows the device to process small fluctuations in resonance in real time. The signal processing and analysis of the feedback ensures that optimal mechanical feedback is achieved.

The device operates at a set frequency of between 20 kHz to 60 kHz, preferably of between 35 kHz and 45 kHz, more preferably of between 37 kHz and 43 kHz and most preferably around 40 kHz. The device also operates at a desired low power, for example in a range of 1 W to 5 W, to reduce the risk of vessel trauma or dissection. In addition to automated control over the desired low-power range of say 1 W to 5 W, the output of the device can be controlled to allow the user to amplify power beyond this range and so to compensate for unexpected interference and to ensure fast effective crossing. The device can therefore also effect a maximum load at higher power levels, for example up to 50 W to 100 W to cross challenging lesions assertively, and to overcome attenuation or deflection of the tip.

Another objective purpose to the procedure is to employ methods to interrogate the feedback signals to characterise the lesion through which the wire is crossing and to collect data on the lesion being crossed, such as its length and composition, which are facets that inform the manner in which the target lesion may be treated by the physician.

This data is also provided as feedback to the physician in a haptic and or visual or audio form on the display to allow the physician to operate the device. For example in one embodiment, this feedback could allow the physician to monitor the crossing, using a simple backlit screen on the compact housing unit and to assess the character of the lesion.

In another embodiment, where the user has access to a network, the data from the procedure may be anonymously captured, to protect patient confidentiality, and communicated from the device to a data storage and processing platform where it may be analysed in real time or later.

The characterisation of the lesion may also be presented to the user for their analysis and interpretation in conducting the procedure.

In another embodiment an attachment is used to record and measure the displacement of the wire as it is traverses within the vasculature and mapped against lesion composition from feedback to characterise the lesion properties as a function of displacement through the lesion.

In another embodiment the system is cradled in a displacement drive that can push the wire over controlled distances to provide for semi-automated and robotic crossing of lesions and a more accurate characterisation of their composition versus displacement.

In another embodiment the active wire is cradled in a slip-lock mechanism where the wire may travel through the centre of the main body of the transducer but there is a lock in the transducer, for example at its distal end, where the transmission of energy is effected.

In another mechanism the activation unit may travel along the length of the wire and locate at a desired point to lock and effect transmission through the slip-lock mechanism.

BRIEF DESCRIPTION OF THE DRAWINGS

In order that the invention may be more readily understood, reference will now be made, by way of example, to the accompanying drawings in which:

FIGS. 25a to 25c are schematic side views, and FIG. 25d is a schematic perspective view, of a further variant of the arrangement shown in FIGS. 23a to 23c, where the active wire exits the horn/transducer assembly through a side port;

FIGS. 26a to 26c are schematic side views, and FIG. 26d is a schematic detail view, of a variant of the arrangement shown in FIGS. 25a to 25c, where the active wire can be removed laterally from the horn/transducer assembly in a direction transverse to the longitudinal axis of the active wire;

FIGS. 42a to 42c are schematic side views that show a wire of the invention being used initially as an active wire to cross a lesion and then as a guide wire to transport a follow-on device to the lesion.

DETAILED DESCRIPTION OF THE INVENTION

Figure 1:
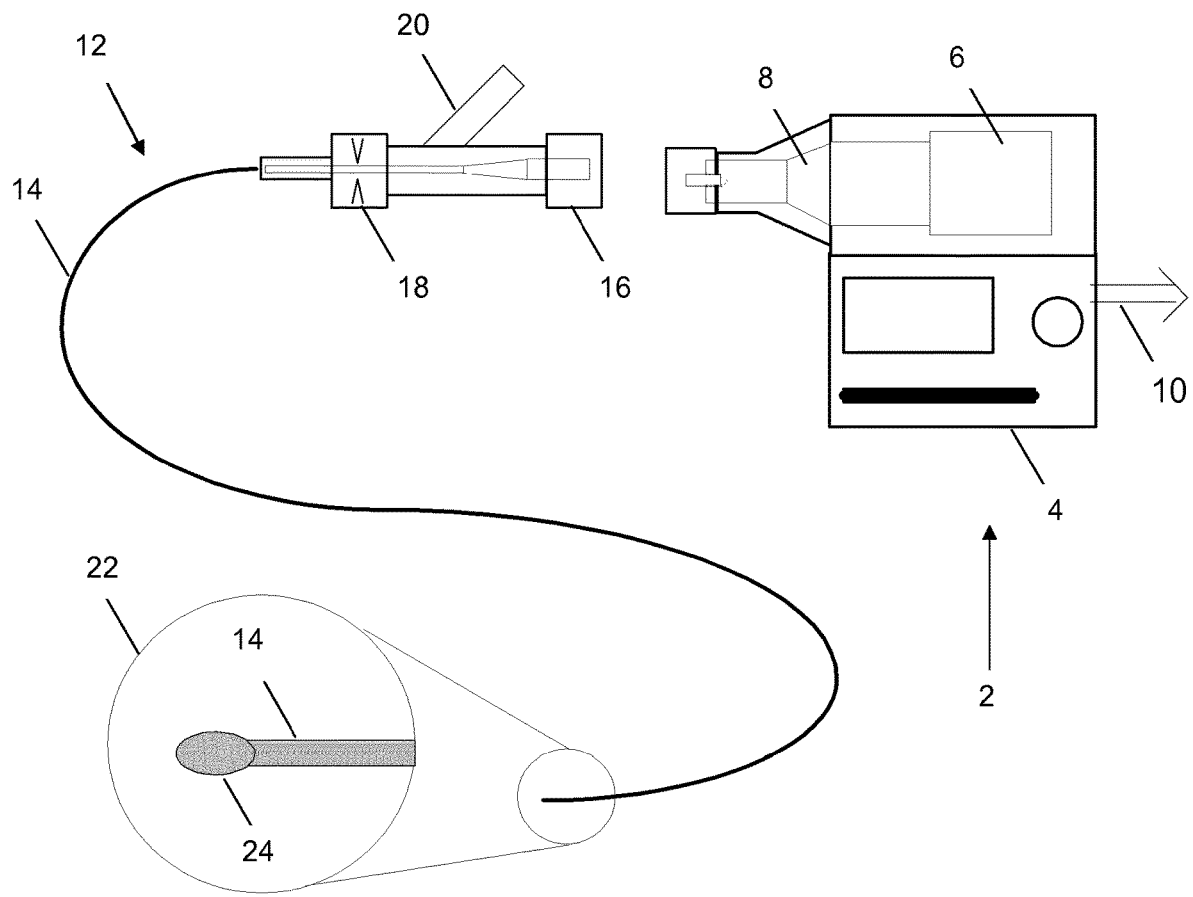
FIG. 1 is a schematic view of a system in accordance with the invention, including a compact housing unit.

FIG. 1 includes a schematic view of a compact housing unit 2. In this configuration the compact housing unit 2 includes an ultrasonic generator 4, an ultrasonic transducer 6 and an acoustic horn 8. The housing unit 2 is connected to an available electricity supply via a power cable 10.

FIG. 1 also shows an active crossing wire assembly 12 that can be connected to the housing unit 2. The active wire assembly 12 comprises a flexible transmission member in the form of a wire 14.

A proximal section of the active crossing wire assembly 12 includes an attachment module 16 and a decoupling module 18 and provides for one or more additional ports 20. A distal section of the active crossing wire assembly 12 is also shown, including an enlarged view 22 of the distal tip 24 of the wire 14. In this example, the distal tip 24 is bulbous.

When coupled and activated, the transducer 6 and the wire 14 vibrate with sufficient amplitude at a proximal end that the distal end of the wire 14 is able to effect crossing of a lesion by virtue of energy transmitted along the wire 14.

The wire 14 may, for example, be more than 2 m in length. For example, access to a lesion in or through the foot may involve the wire 14 travelling a distance of typically 1200 mm to 2000 mm within the vasculature depending on whether an ipselateral or contralateral approach is chosen. In this respect, a wire 14 tapering distally to a fine wire at its tip can navigate to the pedal arteries and around the pedal arch between the dorsal and plantar arteries. However, the invention is not limited to pedal or other peripheral applications and could, for example, be used in coronary applications, where the ability of the wire 14 to navigate to and excavate tortuous small diameter arteries is also beneficial.

Figure 2:
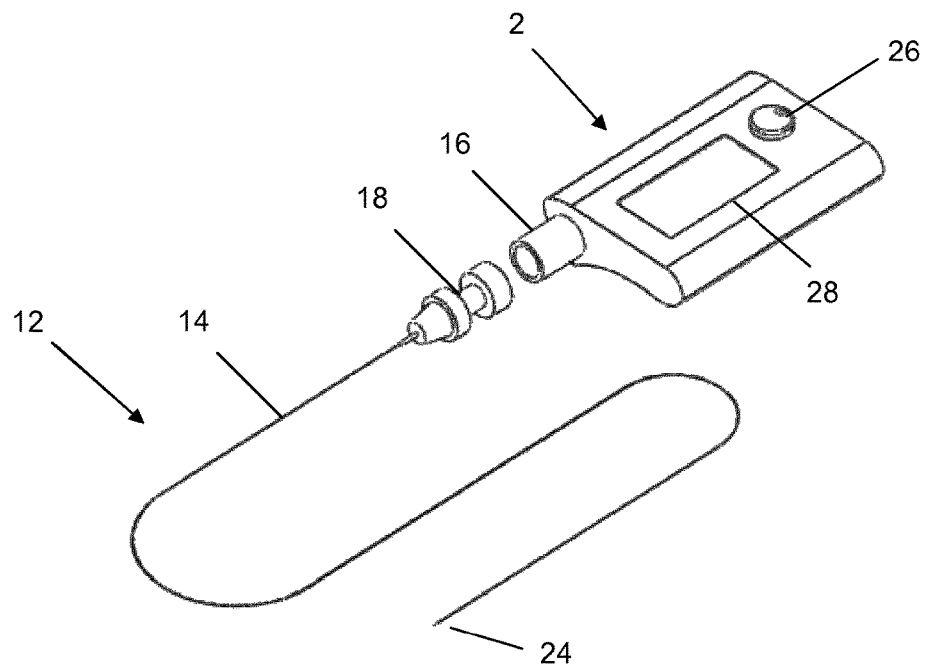
FIG. 2 is a perspective view of the system shown in FIG. 1.

FIG. 2 also shows the compact housing unit 2 and the active crossing wire assembly 12. Also shown are user input controls 26 and a means for providing feedback to a user, exemplified here by a display 28.

The wire 14 may be coupled to the transducer 6 via the acoustic horn 8 or may instead be coupled directly to the transducer 6, in which case the acoustic horn 8 may be omitted. For example, referring to FIG. 2, an attachment module 16 may attach the wire 14 directly to the transducer 6 within the body of the housing unit 2, beneath the display 28 of the housing unit 2.

Figure 3:
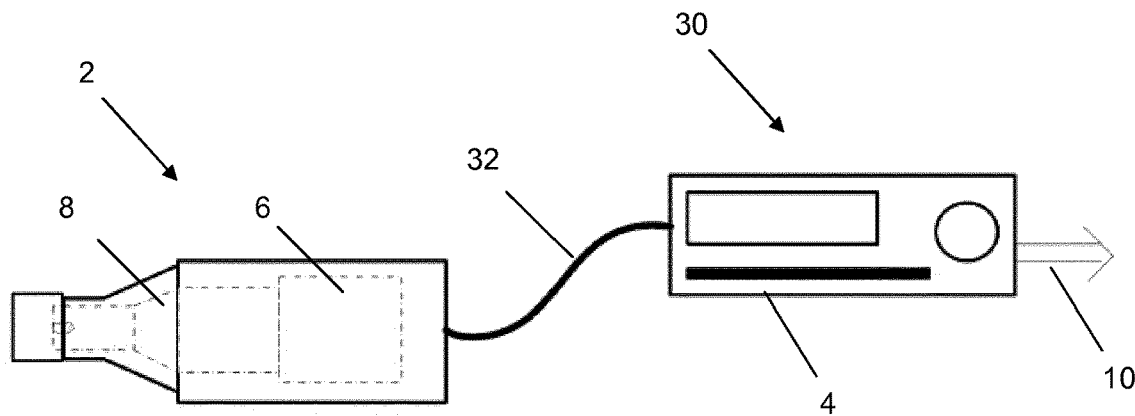
FIG. 3 is a schematic side view that shows another embodiment in which the ultrasonic generator is housed in a separate unit.

FIG. 3 shows a variant in which the ultrasonic transducer 6 and the acoustic horn 8 are integrated into the compact housing unit 2 whereas the ultrasonic generator and circuitry 4 are housed in a separate generator housing unit 30. In this instance, the housing unit is connected to the generator housing unit via a connector cable 32.

Figure 4:
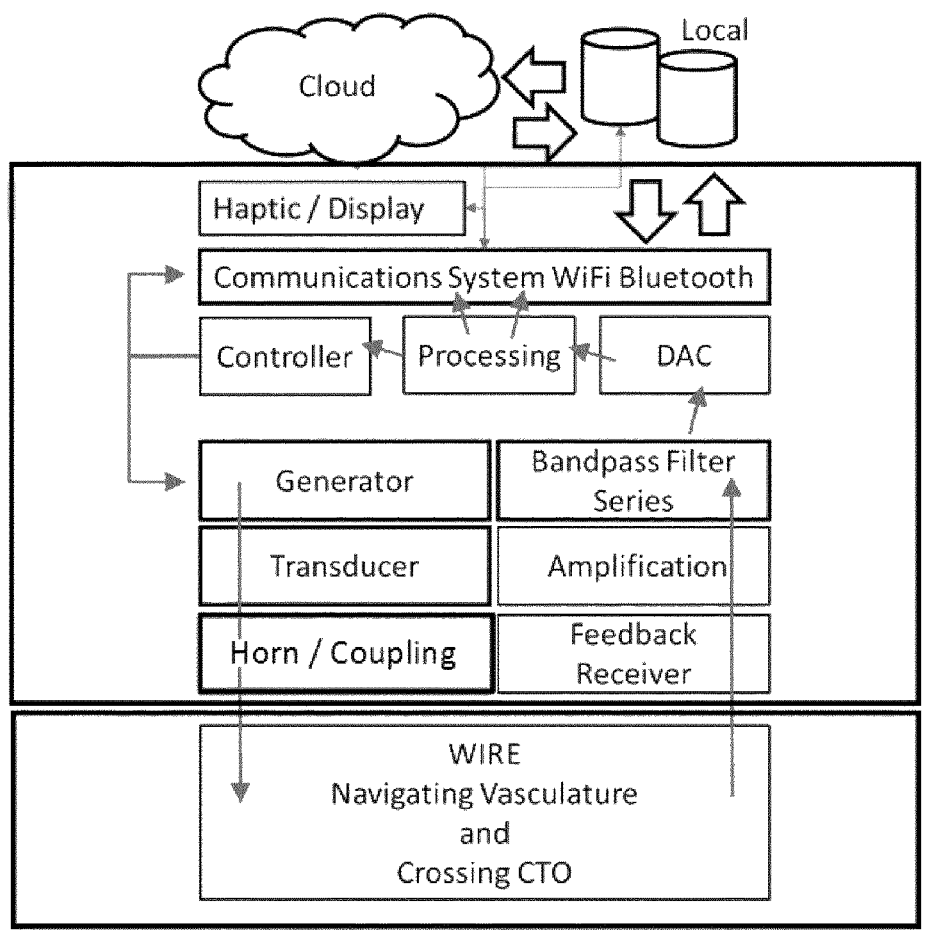
FIG. 4 is a diagram that shows the analog and digital data flow in the system.

FIG. 4 illustrates the components and elements of the system and the flow of data through the system, including communications. A controller within the housing unit controls the ultrasonic generator to generate a signal that is converted to ultrasonic energy by the transducer. The ultrasonic energy is fed via the optional acoustic horn to the active wire that navigates the vasculature and crosses a blockage such as a chronic total occlusion (CTO).

Feedback from the active wire is received by a feedback receiver, amplified by an amplifier and filtered by a series of bandpass filters before passing through analog-to-digital conversion to generate feedback data that is sent to a processor. The controller controls a preferably wireless communications system, for example using a Wi-Fi network or a Bluetooth connection, to receive data from the processor and to communicate that data from the housing unit to local storage and/or to the cloud. FIG. 4 also shows means in the housing unit for providing feedback to a user, such as the aforementioned display and/or a haptic feedback system.

Figure 5:
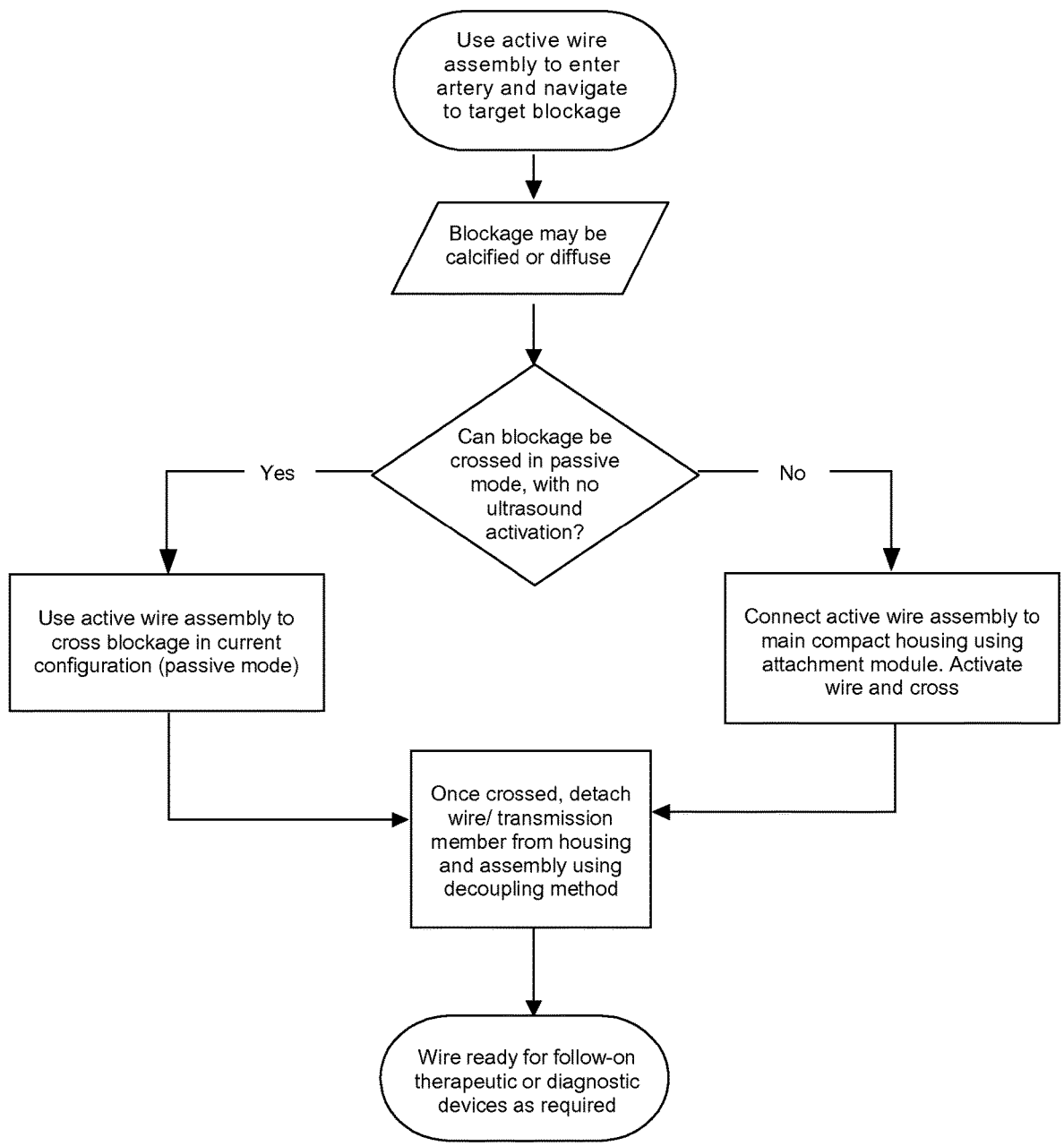
FIG. 5 is a flow chart showing a preferred method of operation of the system.

Turning next to FIG. 5, this shows that the system can be used in a passive or active mode. Initially, the active wire assembly is introduced into an artery and the distal tip of the wire is navigated to a target blockage, which may be calcified or diffuse. If the blockage can be crossed without ultrasound activation of the wire, the system is left in passive mode and the blockage is crossed. Conversely if the blockage cannot be crossed without ultrasound activation of the wire, the active wire assembly is connected to the housing unit and is then activated ultrasonically to effect crossing.

Once the blockage has been crossed, the active wire assembly is disconnected from the housing unit. The wire is then ready to serve as a guide wire to facilitate the introduction and navigation of follow-on therapeutic or diagnostic devices as required.

Figure 6:
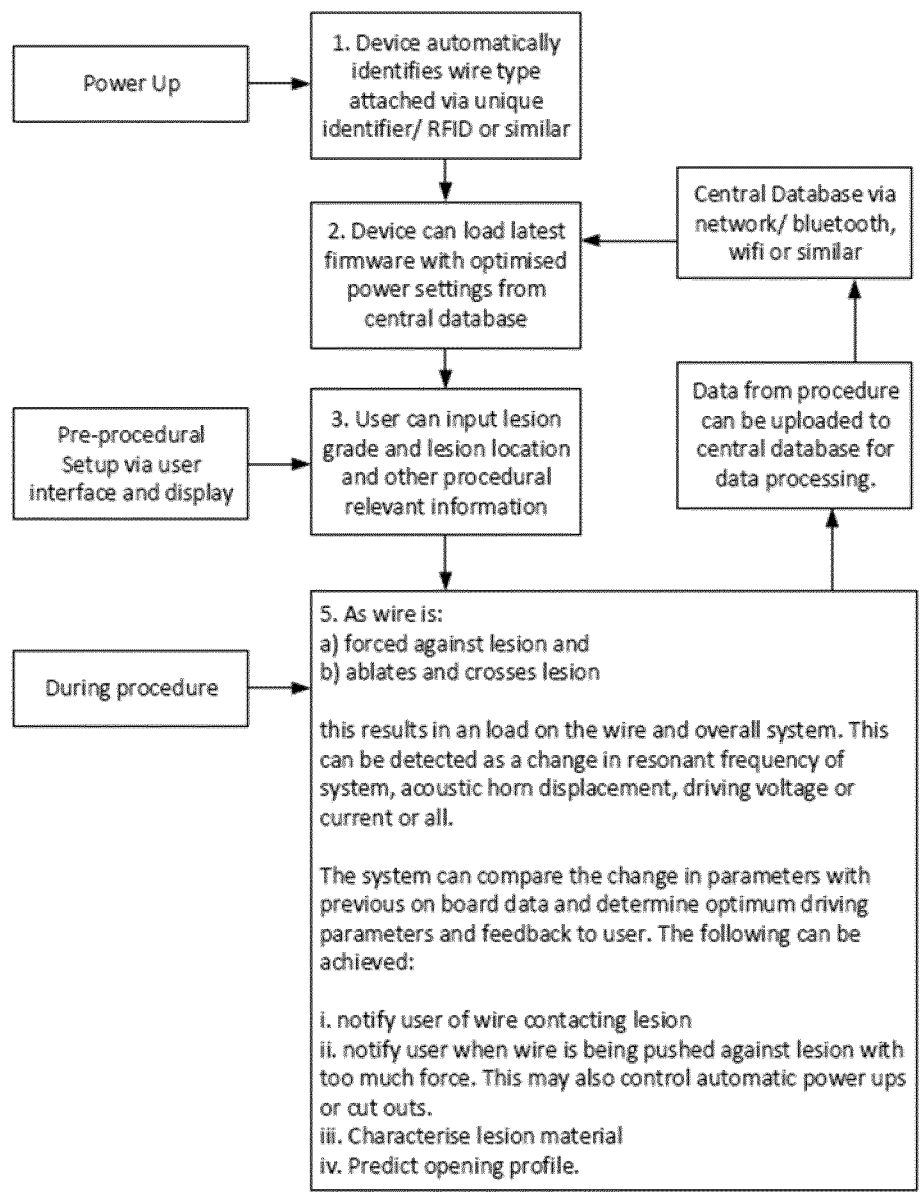
FIG. 6 is a diagram that shows the operational functional flow of the system.

FIG. 6 further summarises the operation of the system and the procedure and the decision points associated with use of the system.

Figure 7:
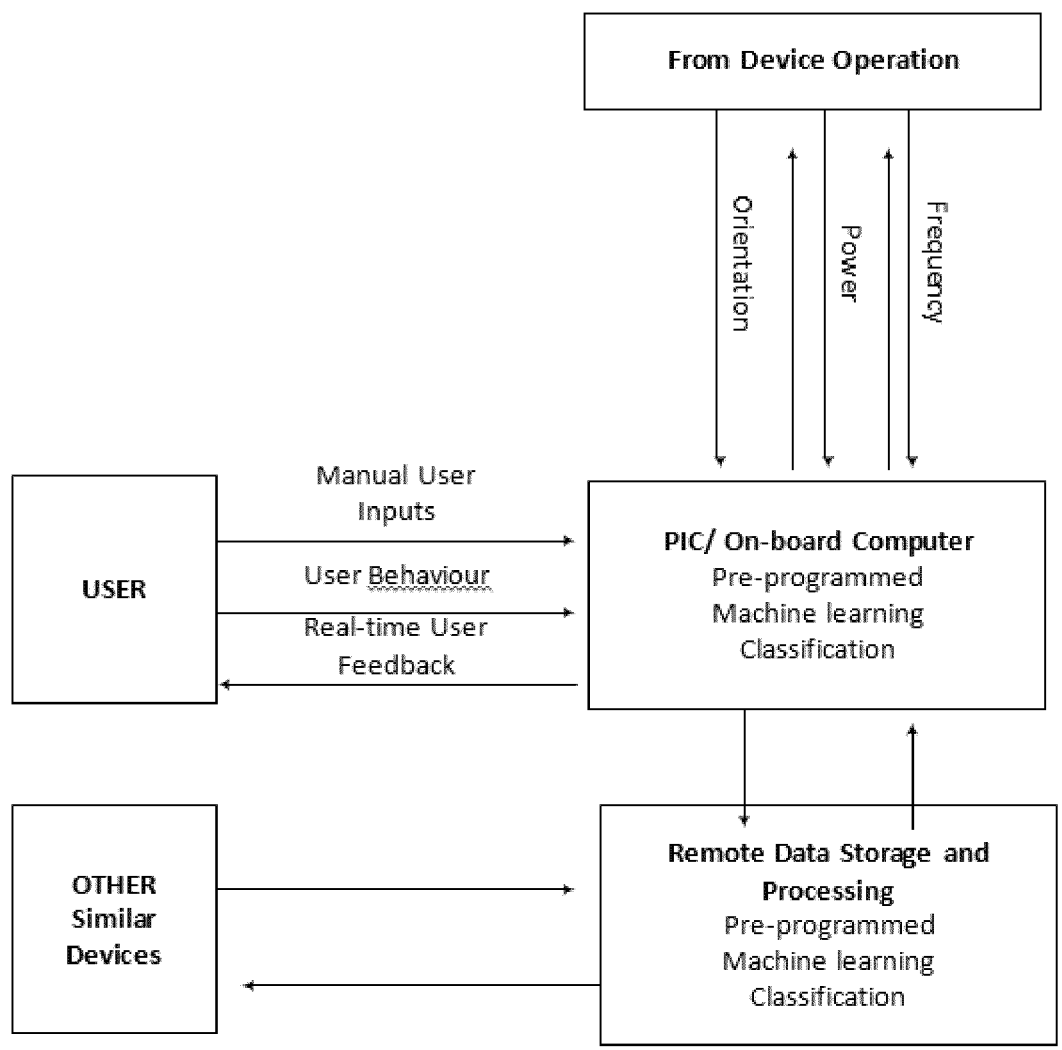
FIG. 7 is a flow chart showing the operation of a semi-autonomous and intelligent control system of the invention.

FIG. 7 is a flow chart that summarises semi-autonomous control of the system. In practice, the system can gather data input by a user prior to operation, such as the anticipated lesion type and its anatomical location. This data can be coupled with real-time inputs as the active wire crosses the lesion, such as power requirements.

Automatically, the system can sense changes in frequency and power and using on-board algorithms can optimise the performance of the active wire. This information can be fed back to the user via haptic, visual or audio means, such as the display on the housing unit.

The variation in the magnitude of the input and control parameters of current, voltage and frequency with the characteristic capacitance of the converter provide a matrix of measurements and controls that are used to determine the power required and to characterise the lesion being crossed.

As the input is kept constant, a variation in current is indicative of the strain energy absorbed or the damping effect along the wire and especially the distal tip of the wire as it crosses the lesion at the sustained frequency of the system.

Monitoring current allows behaviour of the wire to be interpreted and modulation of the voltage allows for the amplification of power and the recovery of frequency as the wire actuates the contact surface and reduces the offset. This array of measurements in the small-frequency range then allows for gross characterisation of the composition of the lesion, be it calcified, fibrous or gelatinous over its entire length.

These interpolated characteristic components are not absolute characteristics of the lesion but are indicative of its composition and consistency, such as: calcific, rigid compacted or disaggregated; or compacted calcific particulate versus non-compacted fibrotic versus hard or soft gelatinous. These characteristics can be indicative of the nature and severity of the lesion and inform the clinician of the optimal therapy to consider.

The system can also both transmit this data and receive optimised performance algorithms via existing wireless or wired communication networks.

Figure 8A:
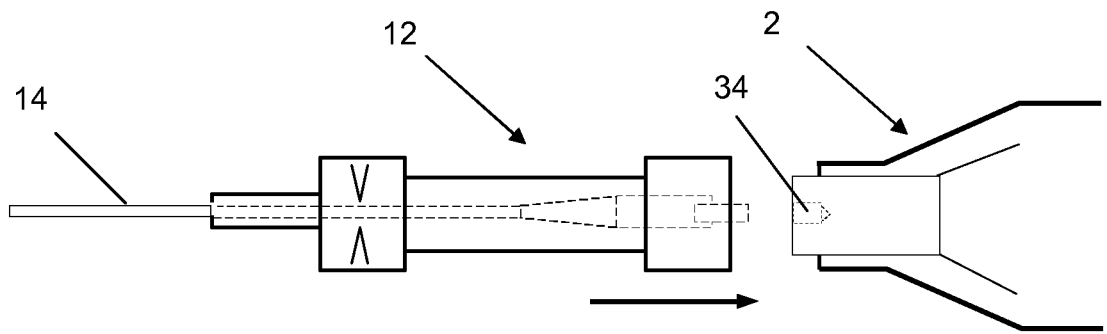
FIGS. 8a, 8b and 8c are schematic side views that illustrate the active wire assembly prior to connection to the horn, then connected to the horn using an appropriate mechanical coupling method, and decoupled from the main housing and proximal assembly by means of a decoupling method.
Figure 8B:
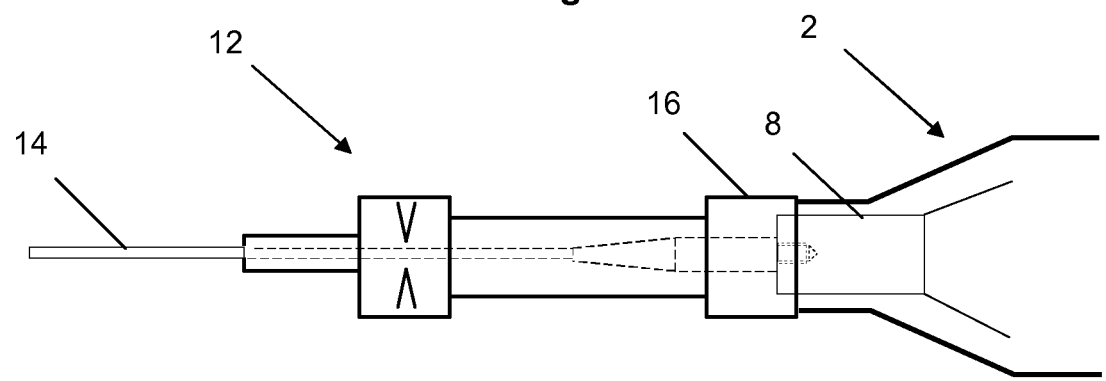
Figure 8C:
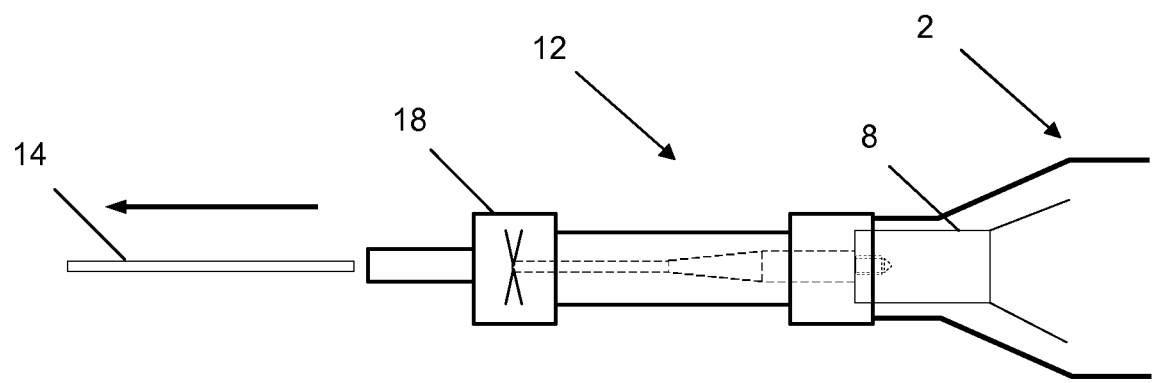

FIGS. 8a to 8c show a method of attachment, where initially the active crossing wire assembly 12 and the compact housing unit 2 are not mechanically coupled together. In this configuration, as shown in FIG. 8a, the wire 14 can be used as a conventional guidewire in its passive mode i.e. without ultrasonic activation.

FIG. 8b shows how, if and when required, the active crossing wire assembly 12 can be mechanically coupled to the housing unit 2. In particular, engagement of the attachment module 16 with a distal end of the housing unit 2 effects alignment and mechanical coupling of a proximally-protruding end portion of the wire 14 within a central bore 34 at the distal end of the acoustic horn 8. Once coupled in this way, ultrasonic vibrations can be transmitted from the acoustic horn 8 along the wire 14 to cross through a lesion.

After crossing the lesion, FIG. 8c shows the wire 14 now decoupled from the acoustic horn 8 following operation of the decoupling module 18. Specifically, opposed blades of the decoupling module 18 are brought together around the wire 14 to break or cut the wire 14. The compact housing unit 2 and the proximal section of the active crossing wire assembly 12 can now be removed from the wire 14, hence separating all other components from the wire 14.

Figure 9A:
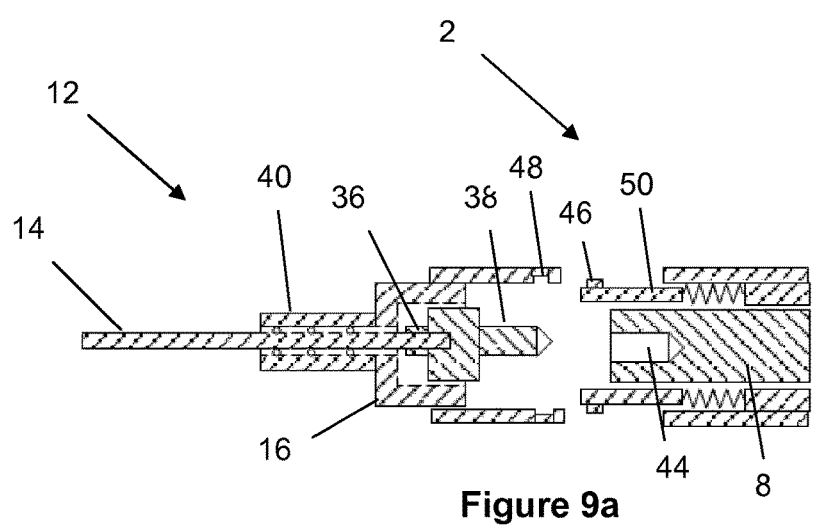
FIGS. 9a, 9b and 9c are sectional views that show an embodiment of a connection method.
Figure 9B:
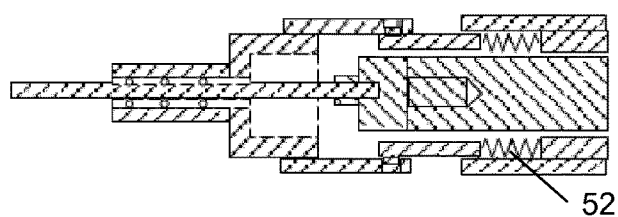
Figure 9C:
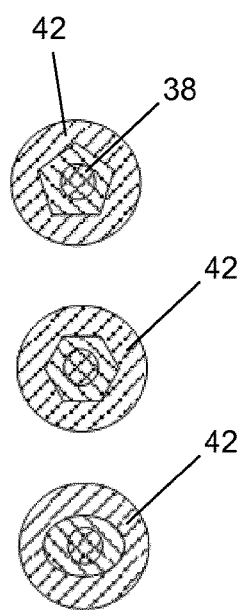

FIGS. 9a to 9c show one embodiment of a proximal section of the active crossing wire assembly 12, in particular the attachment module 16. In this embodiment, the wire 14 is mechanically bonded 36 to a screw connector 38 that comprises an enlarged head and a proximally-extending male thread. The head of the screw connector 38 is gripped and engaged by a surrounding sleeve 40 with a longitudinally-stepped shape. A narrower tubular distal end of the sleeve 40 provides strain relief around the wire 14.

The sleeve 40 and the head of the screw connector 38 are constrained to turn together about the central longitudinal axis of the wire 14. For example, the cross-sectional views of FIG. 9c show that the head of the screw connector 38 may have various rotationally-asymmetrical external shapes 42 that complement, and interlock with, corresponding internal shapes of the sleeve 40. However, relative axial movement is possible between the sleeve 40 and the head of the screw connector 38.

The acoustic horn 8 is shown within the housing unit 2. The acoustic horn 8 comprises a central distal threaded bore 44 that is opposed to, and complements, the male thread of the screw connector 38.

When coupled as shown in FIG. 9b, the proximal section of the active crossing wire assembly 12 axially push-connects to the housing unit 2 via click connectors 46, 48. The click connectors 46 of the housing unit 2 are integral with an axially-retractable tube 50 that is biased distally by springs 52. Retraction of the tube 50 against the bias of the springs 52 allows the male thread of the screw connector 38 to be screwed into the bore 44 of the acoustic horn 8 by turning the sleeve 40, which applies torque to the head of the screw connector 38. Once the thread of the screw connector 38 is fully engaged with the bore 44 of the acoustic horn 8, the sleeve 40 is released and the springs 52 acting on the tube 50 then push the proximal section of the active wire assembly 12, comprising the sleeve 40, clear of the wire 14 and the acoustic horn 8.

Figure 10:
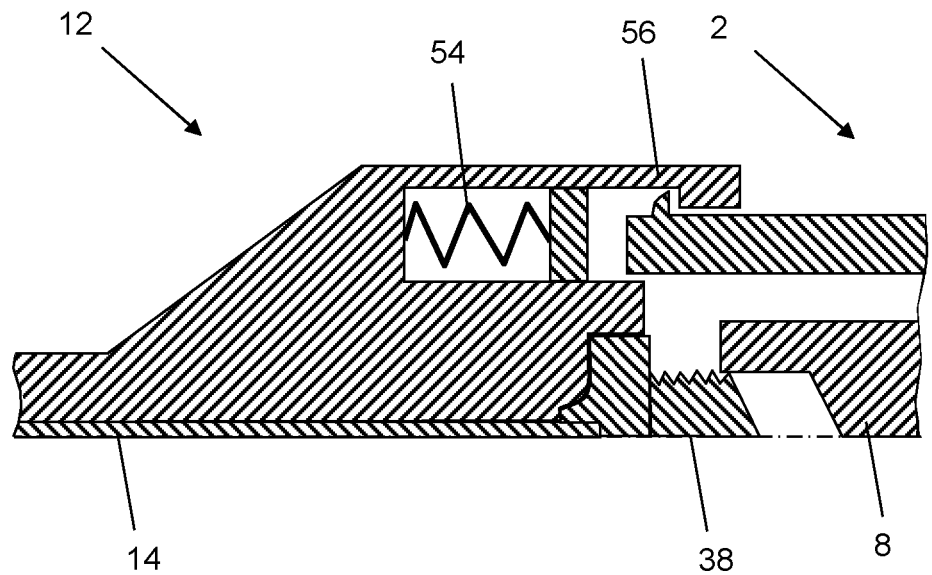
FIGS. 10 and 11 are enlarged partial sectional views that show other embodiments of a linear push-and-screw connection method.
Figure 11:
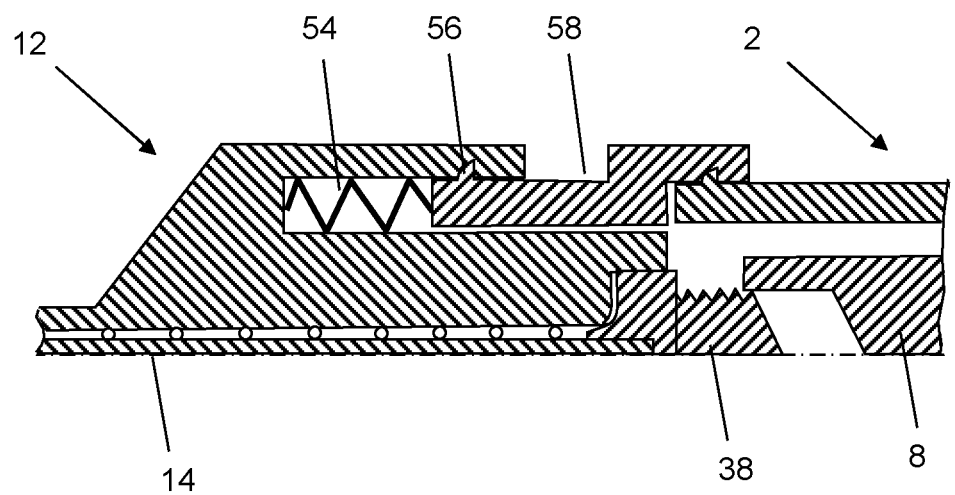

FIG. 10 shows another embodiment of the screw connector, in which a spring mechanism 54 is located in the proximal section of the active wire assembly 12. The screw connector 38 and the wire 14 are shown as before. The active crossing wire assembly 12 and the housing unit 2 are coupled via snap-fit formations 56. FIG. 11 shows a variant of the arrangement of FIG. 10, further comprising a distally-extended snap fit section 58.

Figure 12:
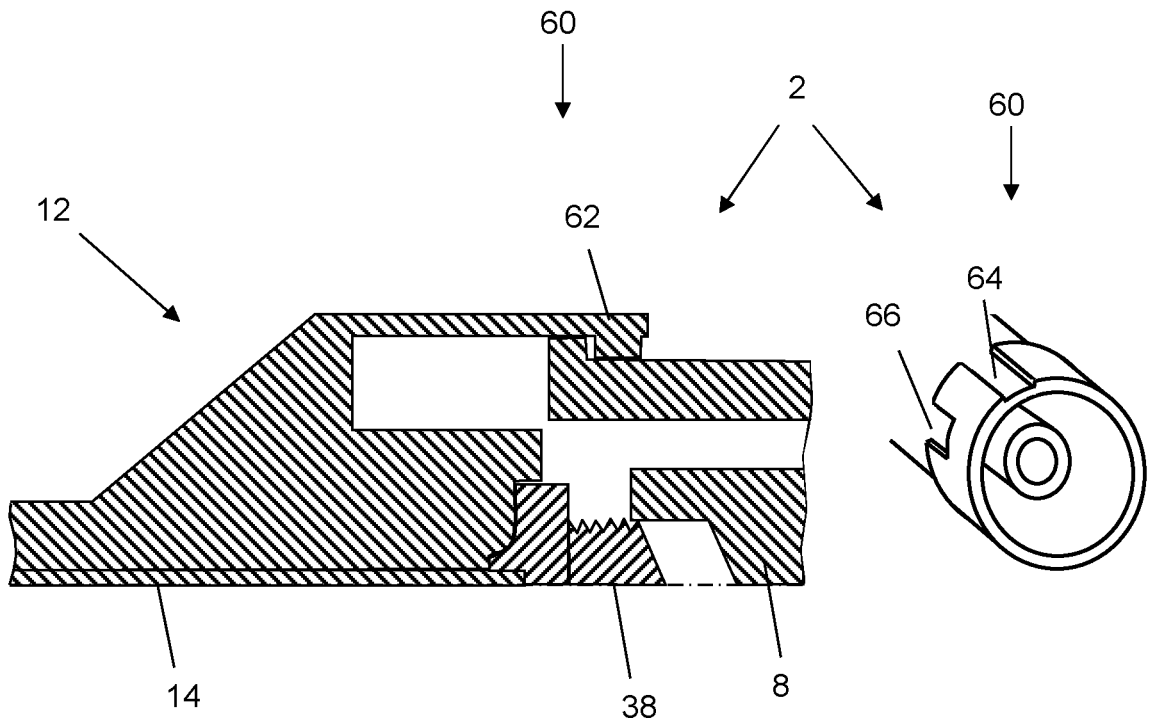
FIG. 12 is an enlarged partial sectional view that shows another embodiment of a connection method that employs mechanical locking.

FIG. 12 shows a screw connector 38 comprising a manual push-screw-pull slotted entry and lock system 60, best appreciated here in the perspective detail view of the distal end of the housing unit 2. The proximal section of the active crossing wire assembly 12 comprises an inwardly-facing lug 62 that initially aligns with an external slot 64 formed in the distal end of the housing unit 2. After the lug 62 travels proximally along the slot 64, the proximal section of the active crossing wire assembly 12 is turned about the central longitudinal axis of the wire 14. This brings the lug 62 into alignment with a notch 66 formed in the distal end of the housing unit. The lug 62 engages distally with the notch 66 to lock the proximal section of the active crossing wire assembly 12 to the distal end of the housing unit 2 as shown in the sectional view of FIG. 12.

Figure 13:
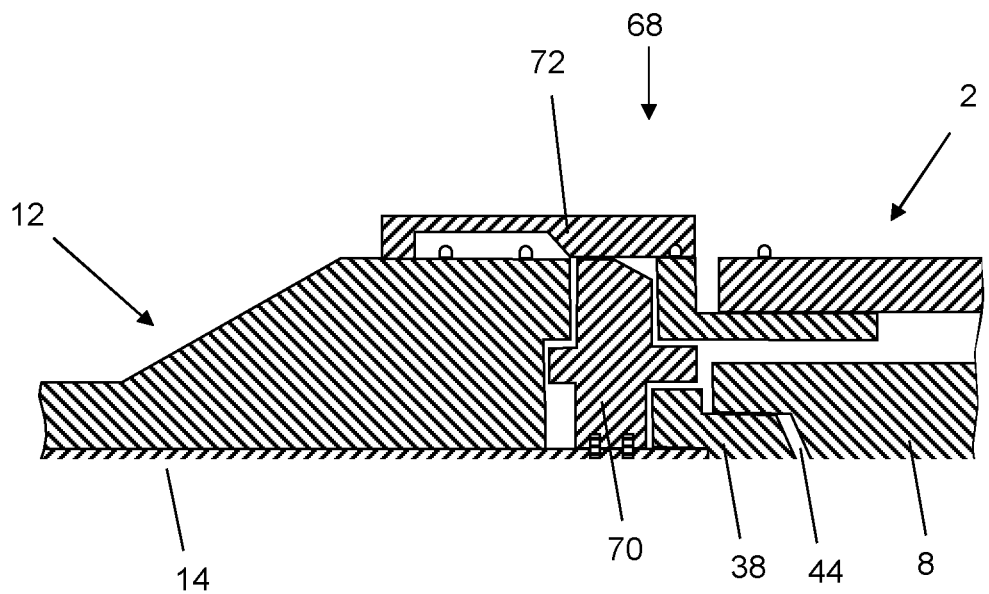
FIG. 13 is an enlarged partial sectional view that shows an embodiment of a screw connection method that employs a radial release mechanism.

FIG. 13 shows a radial connector grip-and-release mechanism 68. The screw connector 38 is held by a radial retainer 70 that is initially held in a radially-inward position by an axially-movable sleeve 72. The retainer 70 transmits torque from the sleeve 72 to the screw connector 38 to screw the male thread of the screw connector 38 into the bore 44 of the acoustic horn 8. Once the screw connector 38 is fully engaged with the acoustic horn 8, sliding the sleeve 72 proximally over the distal section of the housing unit 2 frees the radial retainer 70 to spring radially away from the screw connector 38. This decouples the wire 14 from the sleeve 72 and from the remainder of the proximal section of the active wire assembly 12.

Figure 14:
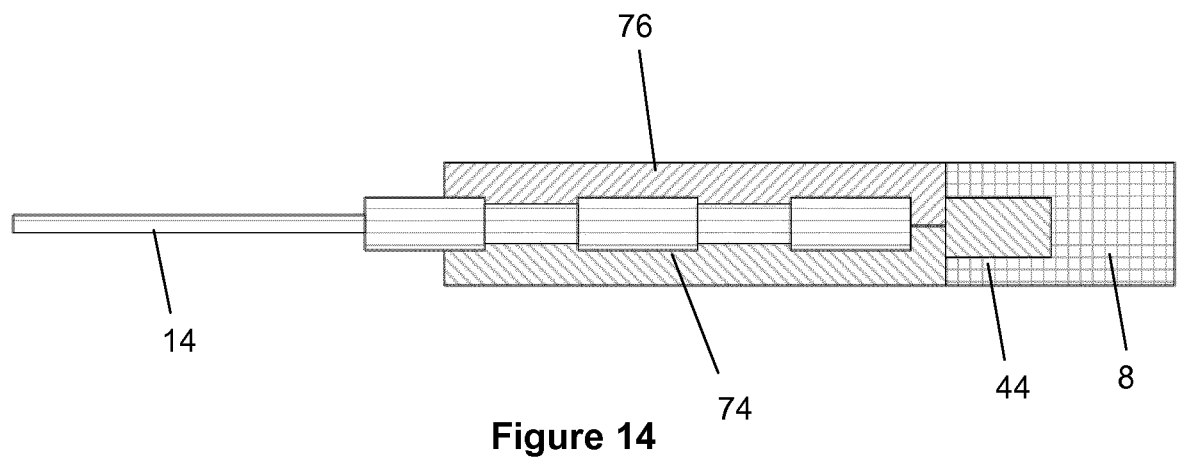
FIG. 14 shows a coupling method with proximal interlocking features on a transmission member.

FIG. 14 shows a connection arrangement in which the proximal end of the wire 14 has a series of geometric features such as circumferential ridges 74 that are embedded within and interlock with a coupling connector 76. The coupling connector 76 has a male screw thread at its proximal end that is engaged with the threaded bore 44 at the distal end of the acoustic horn 8.

Figure 15:
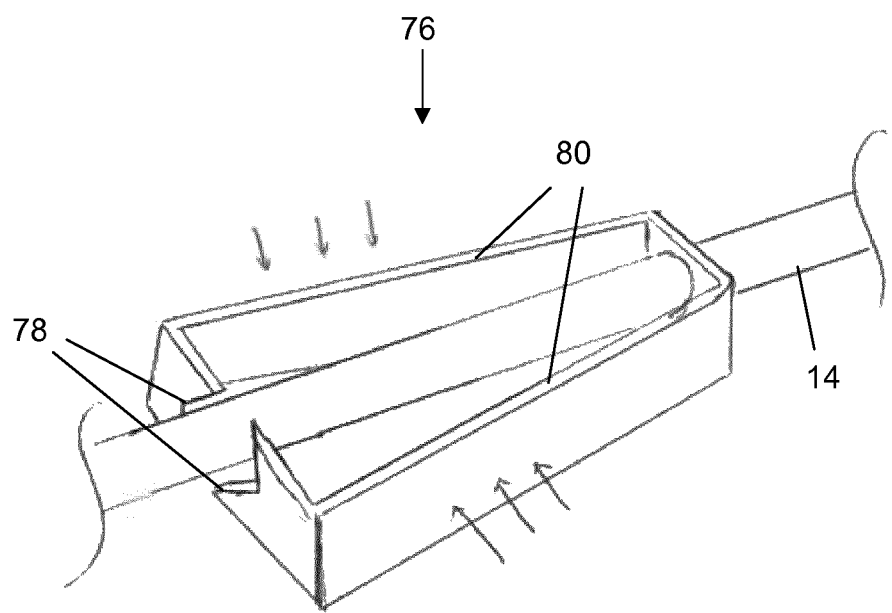
FIG. 15 is a perspective view of a wire release mechanism that fractures or cuts the active wire between opposed blades.
Figure 16:
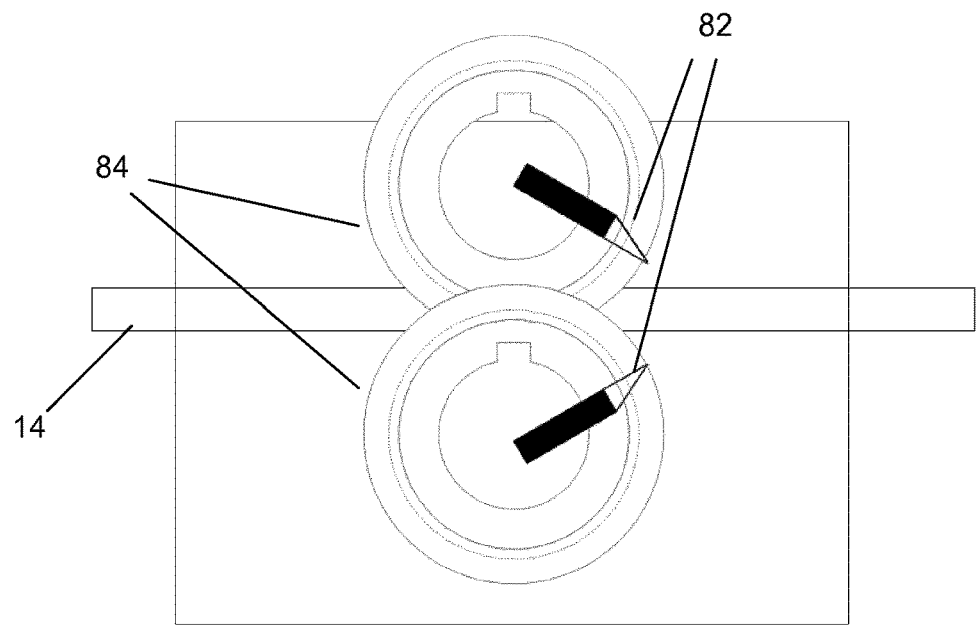
FIG. 16 is a schematic view of a wire release mechanism that fractures or cuts the active wire between blades carried by roller-actuated gears.
Figure 17:
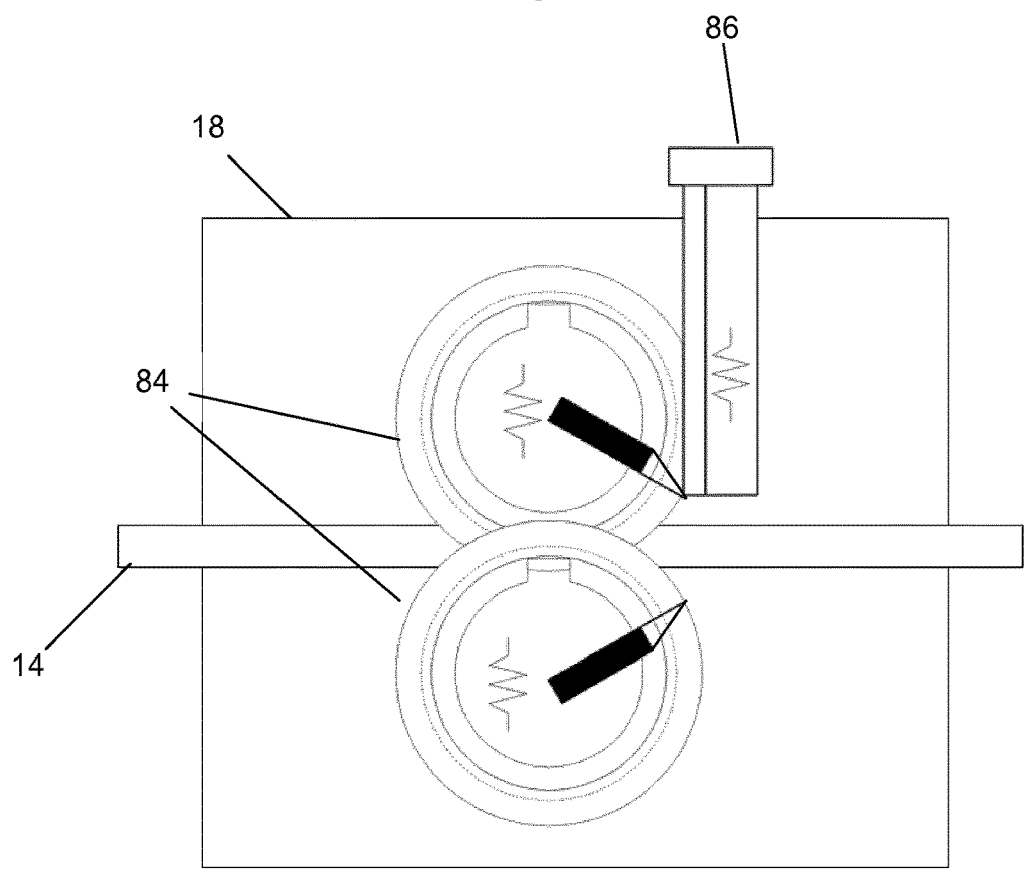
FIG. 17 is a schematic view of a wire release mechanism that fractures or cuts the active wire between blades carried by linearly-actuated gears.

Turning next to FIGS. 15 to 17, these drawings shows show various convenient arrangements for breaking the wire 14 to free the wire 14 from the housing unit 2 after successfully crossing a lesion.

FIG. 15 shows the internal mechanism of a squeeze-action wire-break system 76. A surrounding housing has been omitted for clarity. Here, the wire 14 supports a pair of sharpened blades 78 that are opposed about the wire 14. The blades 78 are integral with resilient levers 80 that, when squeezed together, pinch and sever the wire 14 between the blades 78.

FIGS. 16 and 17 show blades 82 attached to respective meshed gears 84, one gear each side of the wire 14. Opposed rotation of the gears 84 brings the blades 82 together to pinch and cut the wire 14. In FIG. 16, the gears 84 are rotated by a user rolling an exposed side of at least one of the gears 84, which in turn rotates the other gear. Conversely, in FIG. 17, a linear push-button mechanism 86, when depressed, turns one of the gears which in turn rotates the other gear.

Figure 18A:
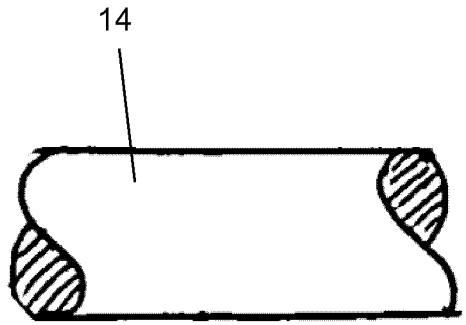
FIGS. 18a to 18c are schematic detail side views that show a method of fracturing an active wire.
Figure 18B:
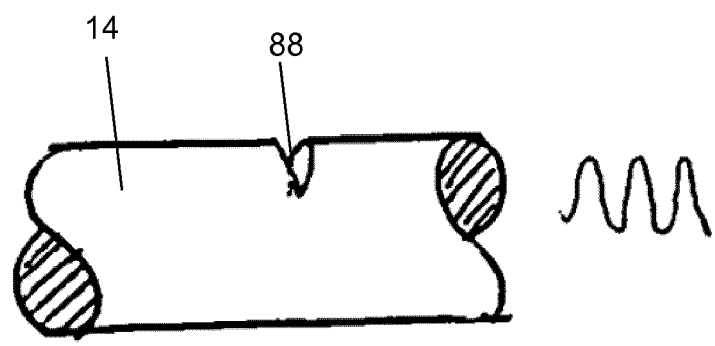
Figure 18C:
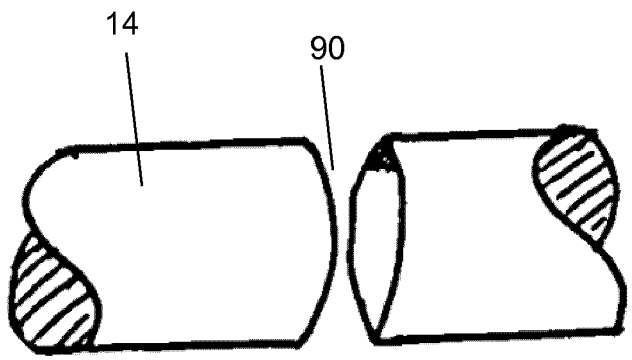

FIGS. 18a to 18c show another approach to breaking the wire. This involves creating a defect of sharpness and applying a cyclical load that causes fatigue.

FIG. 18a shows the wire 14 in its original form with a smooth outer surface, as it will be used to cross a lesion. FIG. 18b shows the wire 14 scored or notched 88, for example with a blade, after crossing the lesion. On then being vibrated by the transducer with sufficient energy at an appropriate frequency, the wire 14 will quickly fracture as shown in FIG. 18c. This is due to propagation of a crack 90 across the diameter of the wire 14 from the transverse score or notch 88, which serves as a point of weakness or stress concentration to initiate the crack 90.

This failure mechanism is apt to be used to detach a crimped nitinol wire by exploiting ultrasonic energy and the intrinsic toughness of the nitinol. Scoring the surface of the wire 14 creates a scratch defect that concentrates stress. As the critical crack length for nitinol is relatively low, ultrasonic loading at high amplitude will cause the wire 14 to break there by creating a perfectly plane strain surface failure.

Figure 19:
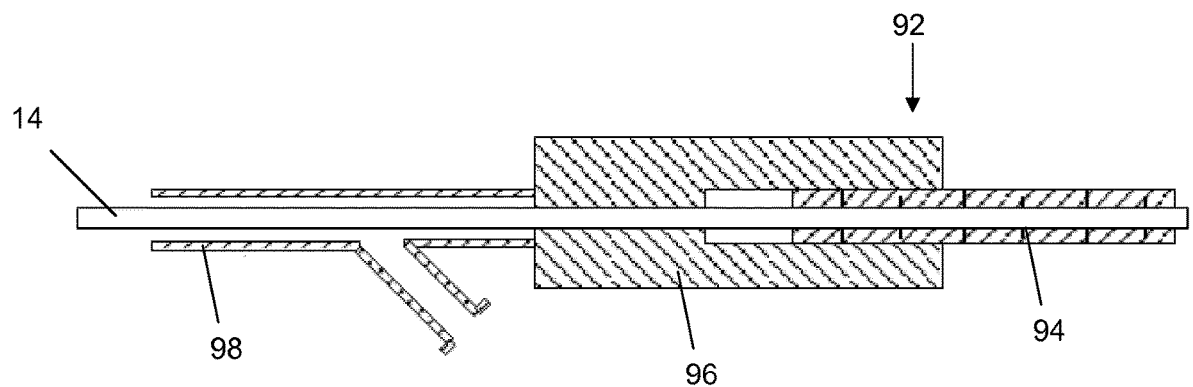
FIG. 19 is a sectional side view of a proximal sub assembly that can measure displacement of the active wire as it traverses.

FIG. 19 shows a measuring attachment 92 that can measure and display the distance over which the wire 14 and a proximal sheath 94 travel longitudinally with respect to a housing 96 and a foresheath 98. In this example, a linear graduated scale is etched, printed or moulded into the proximal sheath 94. An attachment 92 such as this allows the distance of travel of the distal tip of the wire 14 within the vasculature to be measured conveniently at the proximal end of the wire 14.

Figure 20:
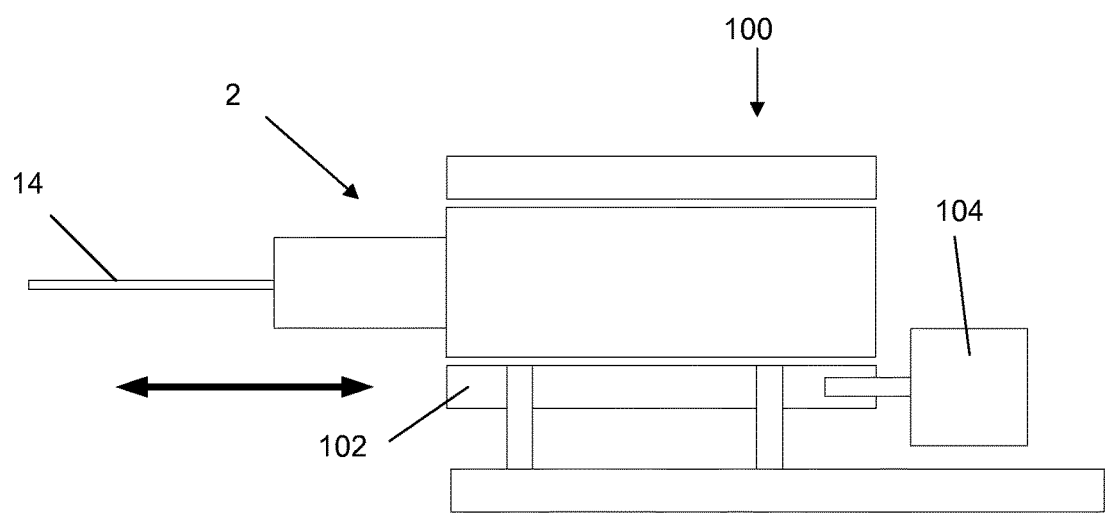
FIG. 20 is a schematic side view that shows the housing unit supported by an automated drive system.

FIG. 20 shows a linear drive system 100 that can cradle or otherwise hold the housing unit 2, and that can advance and retract the housing unit 2 longitudinally as shown. For this purpose, the drive system 100 includes a drive mount 102 and a unit 104 comprising a motor, an encoder and a force sensor unit. The drive system 100 facilitates autonomous or robotic insertion and navigation of the wire 14 through the vasculature and across a lesion.

Figure 21:
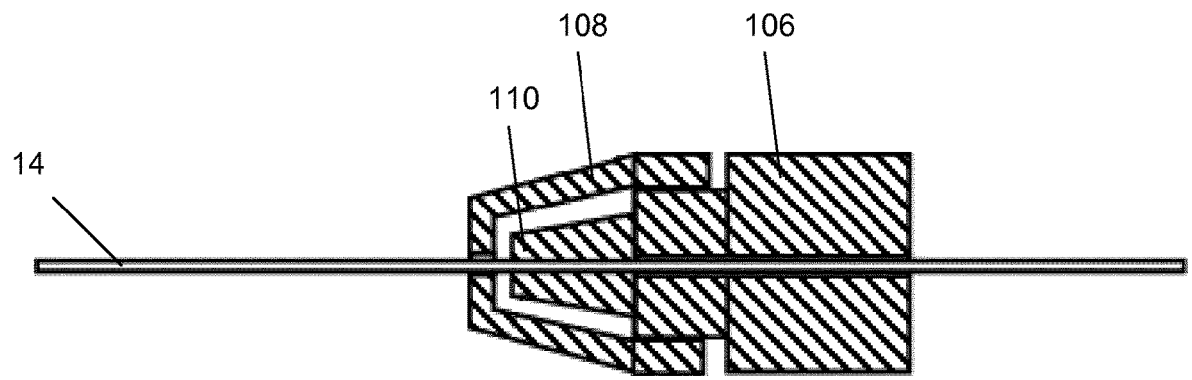
FIG. 21 is a sectional side view of an embodiment in which the acoustic horn and transducer assembly have a hollow port through the full length of the assembly, with an internal wire connect/disconnect mechanism or locking collet.

FIG. 21 shows an active wire 14 passing through a threaded ultrasonic transducer and horn assembly 106. A locking collet 108 has a tapped section that screws onto a thread to close a spring collet clamp 110. The spring collet clamp 110 clamps to the wire 14 over a long interface. This configuration allows for the proximal end of the wire 14 to be fed through the acoustic horn/transducer assembly 106, and to be connected to the assembly 106 at any of multiple points along the length of the wire 14.

Figure 22:
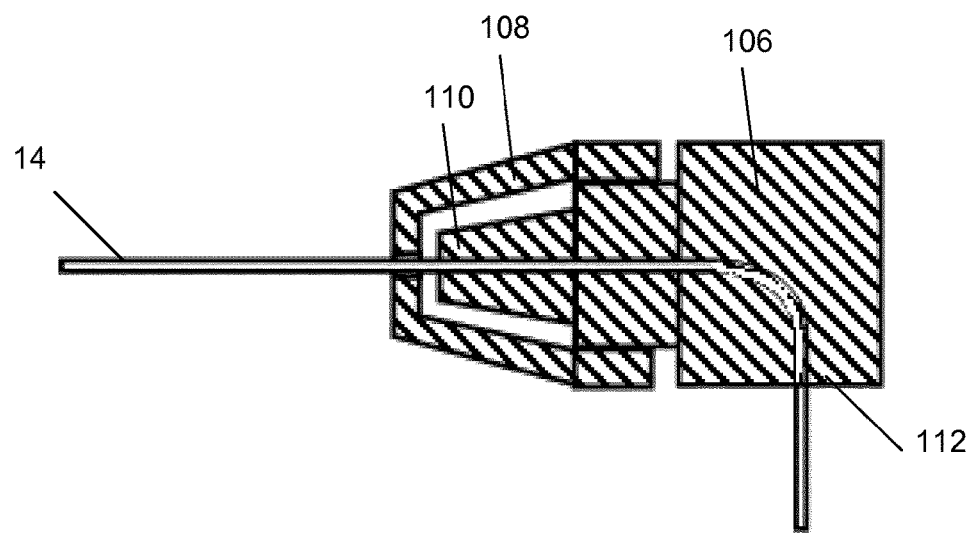
FIG. 22 is a sectional side view of an embodiment in which the acoustic horn/transducer assembly of the activation unit has a hollow port through most of the body length of the assembly but the wire exits the assembly through a side port, enabling the activation unit to lock along the wire through a mechanism in the transducer tip.

FIG. 22 shows a variant of the arrangement of FIG. 21, in which the acoustic horn/transducer assembly 106 has a hollow port through most but not all of the body length of the assembly 106. In this instance, the wire 14 exits through a side port 112, enabling this activation unit to lock at any of multiple points along the wire 14 through a mechanism in the distal tip of the assembly 106.

Figure 23A:
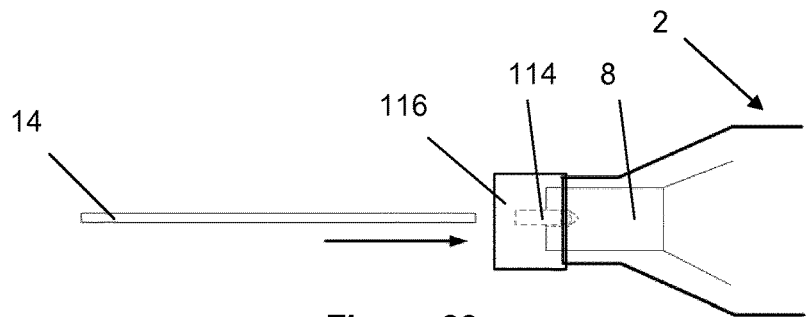
FIGS. 23a to 23c are schematic side views acoustic horn/transducer assembly that show a further method for connecting the active wire.
Figure 23B:
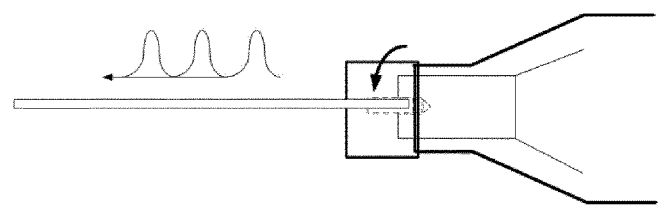
Figure 23C:
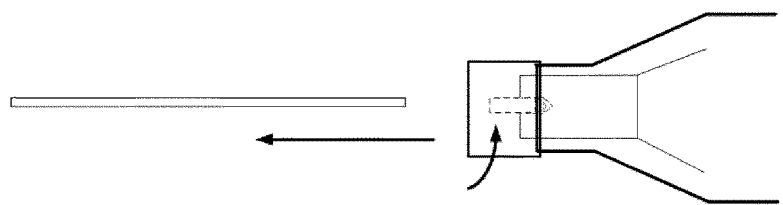

FIGS. 23a to 23c show an arrangement in which a proximal end of the wire 14 is received in a central distal bore 114 of the acoustic horn 8 within the housing 2. After inserting the wire 14 into the bore 114 as shown in FIG. 23a, a twist-lock mechanism 116 on the distal end of the housing 2 is turned to lock the wire 14 to the acoustic horn 8 as shown in FIG. 23b. The acoustic horn 8 can then feed ultrasonic energy into the wire 14 as shown. When there is no longer a need for ultrasonic activation of the wire 14, the wire 14 can be unlocked from the acoustic horn 8 by reversing the twist-lock mechanism 116 and can then be withdrawn longitudinally as shown in FIG. 23c.

FIGS. 24a to 26d illustrate various additional concepts relating to adjustable location activation. They show further arrangements in which an activation system comprising a housing 118 containing a transducer/horn 120 can slide and lock, or 'slip and stick', over the crossing wire 14 and so be coupled to the crossing wire 14 at any location along the proximal portion of the wire 14 outside the patient's body.

Figure 24A:
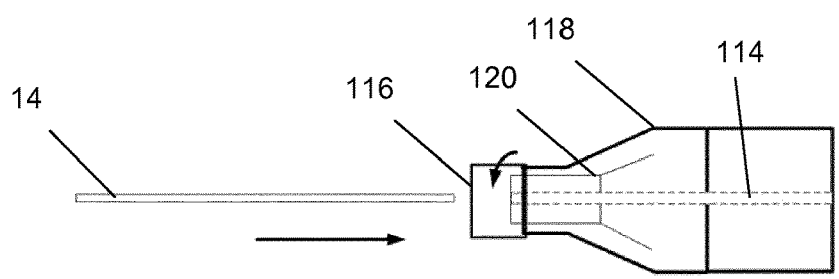
FIGS. 24a to 24c are schematic side views of a variant of the arrangement shown in FIGS. 23a to 23c, where the active wire extends through the full length of the horn/transducer assembly.
Figure 24B:
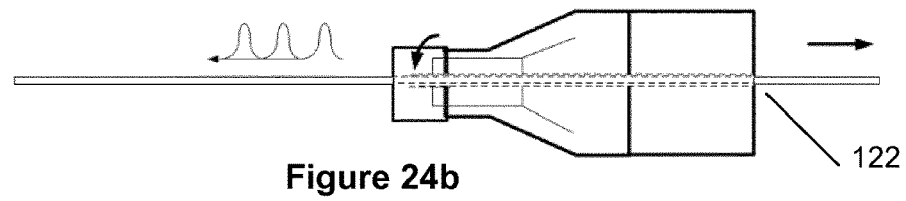
Figure 24C:
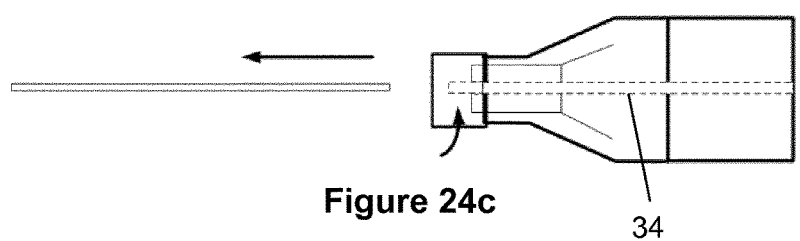

For this purpose, FIGS. 24a to 24c show a variant of the arrangement shown in FIGS. 23a to 23c, in which the central bore 114 in the transducer/horn 120 extends longitudinally through the housing 118 and opens out to both the distal and proximal ends of the housing 118. This allows the wire 14 to extend through and protrude from both ends of the housing 118 as shown in FIG. 24b, thus allowing the housing 118 to be repositioned longitudinally relative to the wire 14.

In this arrangement, the wire 14 is still inserted longitudinally into the distal end of the transducer/horn 120 as shown in FIG. 23a and is withdrawn longitudinally from the distal end of the transducer/horn 120 as shown in FIG. 23c. Again, a twist-lock mechanism 116 on the distal end of the housing 118 is turned to lock the wire 14 to the transducer/horn 120 as shown in FIG. 23b.

FIGS. 25a to 25d show that the wire 14 can emerge from the housing 118 through an opening other than a central opening 122 at the proximal end of the housing 118. In the example shown here, the wire 14 exits the transducer/horn 120 through a lateral port 124 that communicates with the central distal opening of the bore 34. The laterally-exiting part of the wire 126 extends from the port 124 to exit the housing 118 through a lateral opening aligned with the port 124. Thus, the wire 14 deflects from the central longitudinal axis of the transducer/horn 120 through an acute angle to exit the transducer/horn 120 laterally.

As before, the wire 14 is inserted longitudinally into the distal end of the transducer/horn 120 as shown in FIG. 23a and is withdrawn longitudinally from the distal end of the transducer/horn 120 as shown in FIG. 23c. Again, a twist-lock mechanism 116 on the distal end of the housing 118 is turned to lock the wire 14 to the transducer/horn 120 as shown in FIG. 23b.

In a further variant of the lateral-exit principle shown in FIGS. 25a to 25c, FIGS. 26a to 26d show an arrangement in which the wire 14 can be pulled laterally from (and optionally also inserted laterally into) the transducer/horn 120 within the housing 118. The wire 14 is received in a longitudinal slot 130 that can be closed and opened by turning pivotable jaws 128 of the acoustic horn 118 as shown in the detail view of FIG. 26d. When closed, the jaws 128 encircle and engage the wire 14 to couple the wire 14 to the transducer/horn 120. When opened by relative angular movement around the central longitudinal axis, the jaws 128 free the wire 14 from the transducer/horn 120 to exit the transducer/horn 120 through the slot 130. The housing 118 has a corresponding slot 132 that allows the wire to exit the housing 118 laterally to free the wire 14.

As excitation of the wire 14 is only required in the distal direction from the housing 118, damping materials in the housing 118 may prevent or damp excitation of the portion of the wire 14 that extends proximally from the housing 118 in the embodiments shown in FIGS. 24a to 26d. Various, typically elastomeric, materials can be used to effect damping such as a silicone seal or gasket. More generally, unwanted excitation may be damped by contact between the wire 14 and a wall of the housing 118 around a side port of the housing 118.

Figure 27A:
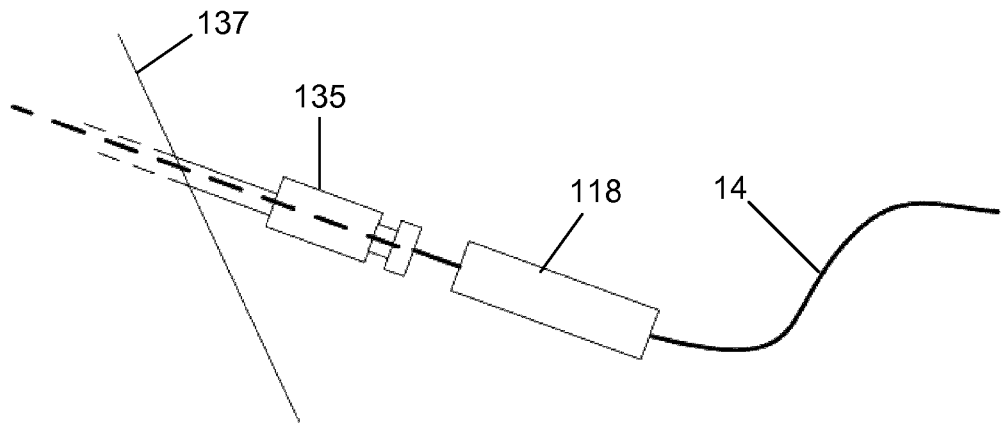
FIGS. 27a to 27c are schematic side views showing the housing unit positioned at various longitudinal positions along a proximal portion of the active wire protruding from a patient's body.
Figure 27B:
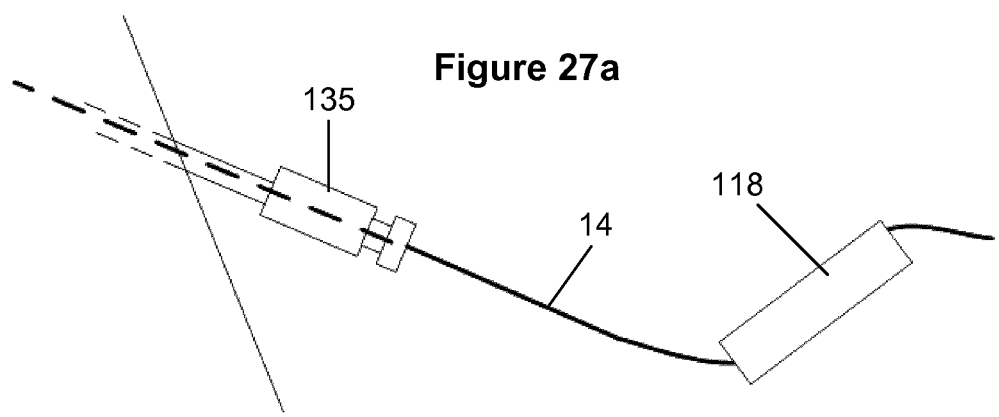
Figure 27C:
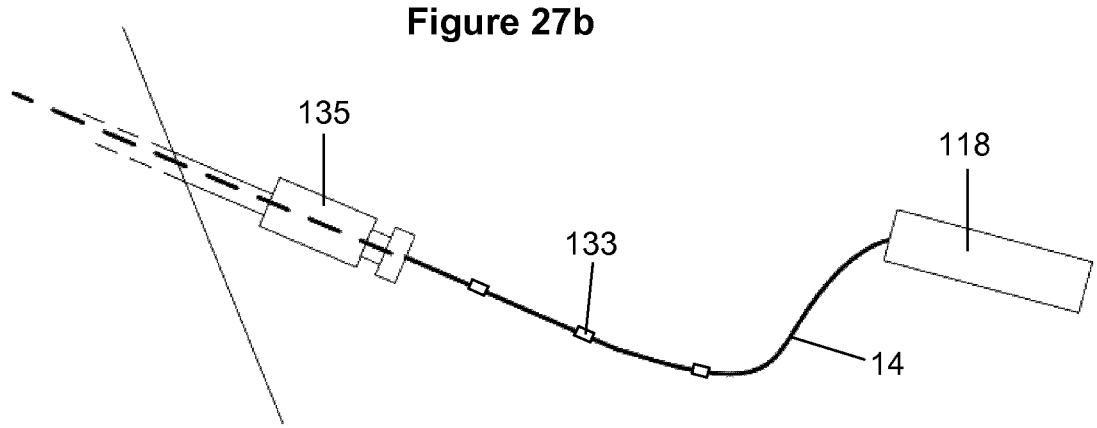

FIGS. 27a to 27c show that a physician can disconnect and reconnect the housing 118 at any location along the external proximal portion of the wire 14, allowing the wire 14 to be loaded and unloaded as required. As shown in FIG. 27c, the wire 14 can be marked at regular or irregular intervals 133 along its length that are characteristic of harmonics at an activation frequency of say 40 kHz, such as $\lambda/2$ and $\lambda/4$.

The housing 118 can be released from the wire 14, relocated at specific longitudinal intervals and reconnected to the wire 14 multiple times as the wire 14 is fed in a forward or distal direction. In general, the housing 118 or the wire 14 may move relative to each other, allowing the physician to move the wire 14 to cross a lesion or to find a better location for the housing 118 at which to activate the wire 14. Removing the housing 118 from the wire 14 and later recoupling it to the wire 14 allows for other devices to be placed on or left on the wire 14 and for the wire 14 not to be moved in the course of a procedure, which greatly enhances the ease of use for the physician.

For example, the housing 118 can be hitched onto the wire 14 close to where the wire 14 enters an introducer sheath 135 and the patient's body 137, as shown in FIG. 27a. FIGS. 27b and 27c show other locations at which the housing 118 can be coupled to the wire 14. FIG. 27b shows the housing at an intermediate location between the introducer sheath 135 and the proximal end of the wire 14, whereas FIG. 27*c* shows the housing 118 at a proximal location at or adjacent to the proximal end of the wire 14.

Turning next to FIGS. 28 to 33, these drawings show various connector concepts whose primary objective is to achieve excellent acoustic coupling between the crossing wire and the rest of the system. In this respect, the transducer and the coupling method have to work in unison. In particular, the transducer, with coupling interface components optionally including an acoustic horn, is designed to resonate at the driving frequency of the system.

The transducer may, for example, be constructed from Grade 5 titanium or aluminium alloy or steel alloy with a step configuration. The shape and dimensions of the transducer are selected to achieve an amplification gain while ensuring that the system remains near to its operating resonant frequency. In addition, any modifications to a distal driving face of the transducer so as to accommodate a connector have to be considered and accounted for with regard to resonant response.

Figure 28:
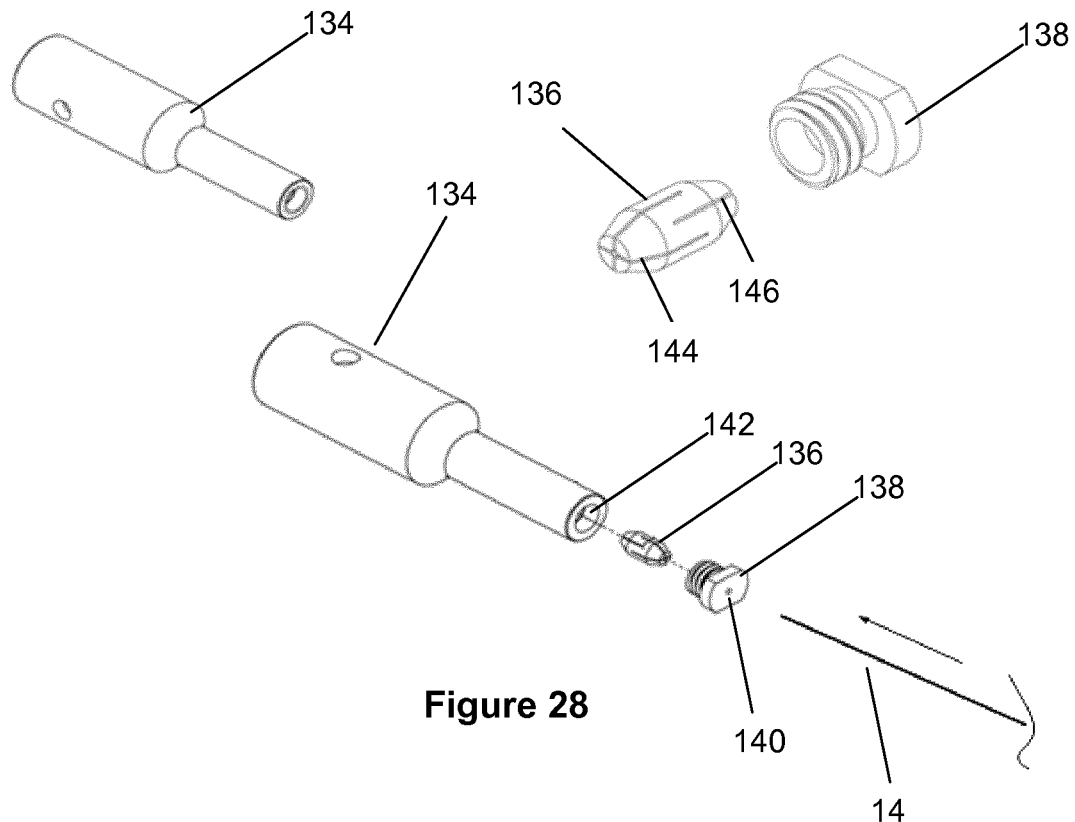
FIGS. 28 to 31 are exploded perspective views of various collet arrangements for securing the active wire to a horn/transducer assembly.

FIG. 28 shows a transducer 134 fitted with a double-taper collet 136 and a cap screw 138. The cap screw 138 has external formations to facilitate gripping and turning by a user.

The wire 14 enters through a central hole 140 in the cap screw 138 opposed to a countersunk base hole 142 in the distal face of the transducer 134. The wire 14 extends through the collet 136, which is interposed between the base hole 142 and the cap screw 138. The taper at the proximal end of the collet 136 complements the countersunk base hole 142. The cap screw 138 similarly receives and complements the taper at the distal end of the collet 136.

The collet 136 comprises a first pair of slits 144 at its proximal end and a second pair of slits 146 at its distal end. Each pair of slits 144, 146 extends longitudinally by more than half of the length of the collet 136. The slits 144, 146 of each pair are in mutually-orthogonal planes that intersect along the central longitudinal axis of the collet 136. The slits of the second pair 146 are rotated about the central longitudinal axis by 45° relative to the slits of the first pair 144.

Torque applied to the cap screw 138 advances the cap screw 138 to compress the collet 136 longitudinally. Consequently, the tapered ends cause, and the slits 144,146 allow, the collet 136 to compress radially to grip the wire 14. Advantageously, the collet 136 provides a substantially uniform loading pattern based upon uniform radial reduction and therefore uniform gripping of the wire 14, improving transmission of energy and fatigue life.

Figure 29:
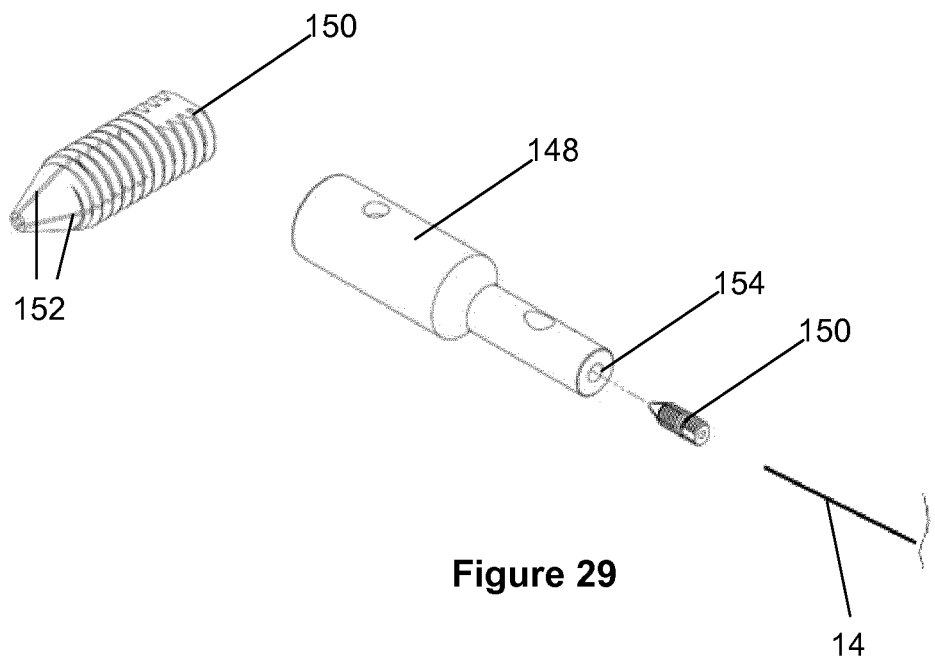

FIG. 29 shows a transducer 148 fitted with a single-taper male-threaded collet 150. The tapered proximal end of the collet 150 has orthogonal slits 152 like the collet 136 of FIG. 28. The collet 150 anchors the wire 14 within a complementary threaded bore 154 in the distal end of the transducer 148 when torque is applied to the collet 150 to advance the collet 150 along the bore 154. A complementary taper at the proximal base of the bore 154 then compresses the collet 150 radially to grip the wire 14.

Figure 30:
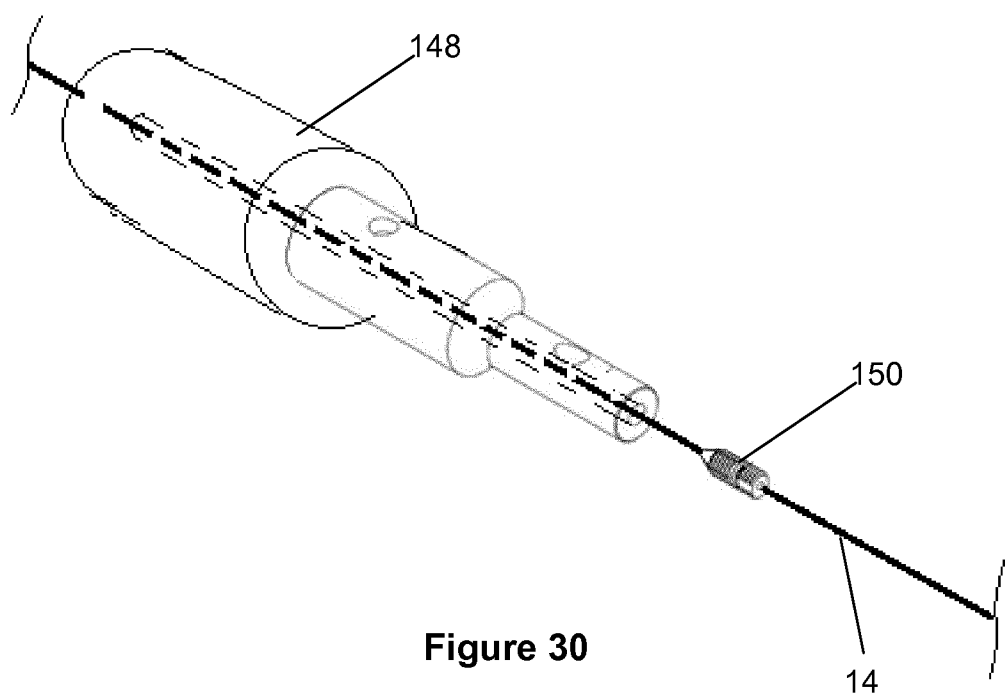

FIG. 30 shows a variant of the arrangement shown in FIG. 29, in which the wire 14 extends through the full length of the transducer 148 from the distal end to emerge from the proximal end.

Figure 31:
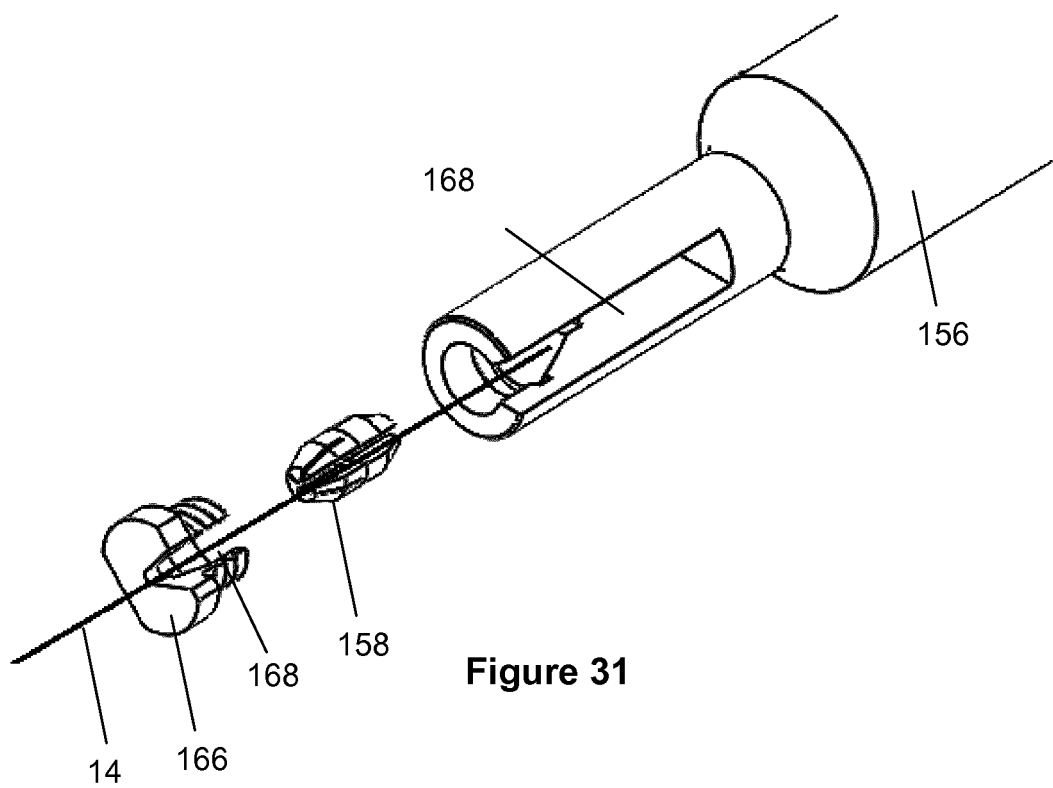
Figure 32A:
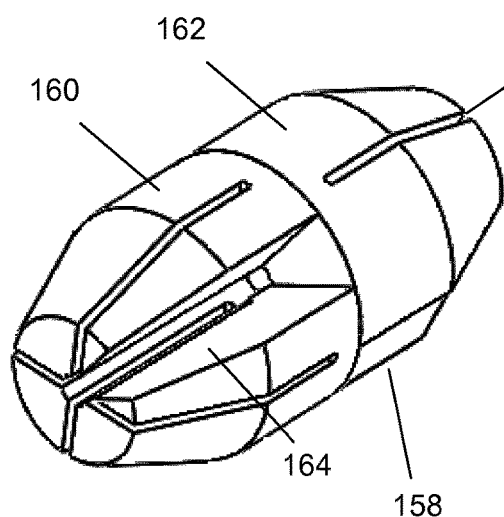
FIGS. 32a and 32b are enlarged perspective views of the collet shown in FIG. 30.
Figure 32B:
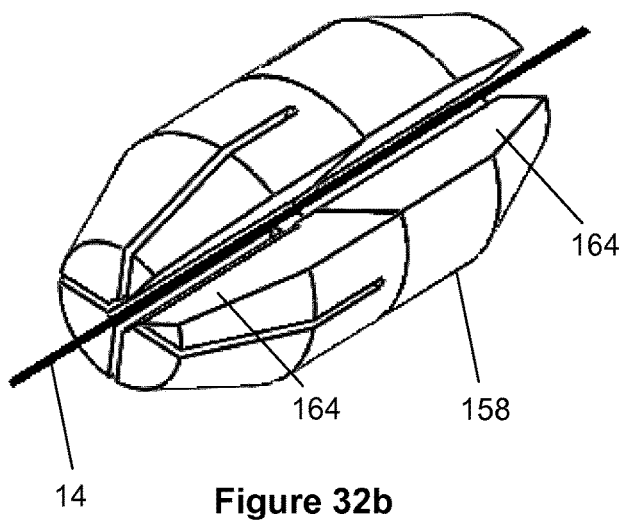

FIGS. 31, 32*a* and 32*b* show a transducer 156 with a double-tapered counter-locking wire release collet 158. The counter-locking system embodies the concept of mutual alignment and misalignment between twin longitudinally-split collet parts 160, 162 that can turn relative to each other about a common central longitudinal axis. When longitudinal slots 164 in the collet parts 160, 162 are misaligned as shown in FIG. 32*a*, the wire 14 is trapped within the collet 158. Conversely, when longitudinal slots 164 in the collet parts 160, 162 are aligned as shown in FIG. 32*b*, the wire 14 is freed from the collet 158 to be able to exit the collet 158 in a direction transverse to the central longitudinal axis of the collet 158.

Correspondingly, the cap screw 166 and the transducer 156 comprise slots 168 that can be aligned to free the wire 14 for lateral removal from the transducer 156, or for lateral insertion, in the manner of the embodiment shown in FIG. 26*c*.

The principle here is that the wire 14 may be released from the collet 158 as the clamping torque force is released and as the slots 164 in the parts 160,162 of the collet 158 are brought into alignment with each other and with the slots 168 in the cap screw 166 and the transducer 156. This is achieved by anchoring the proximal part 162 of the collet 158 to the transducer 156 and applying torque from the cap screw 166 to the distal part 160 of the collet 158 as the cap screw 166 is turned to release the clamping force.

The proximal part 162 of the collet 158 may, for example, locate onto a spline formation of the transducer 156 to align and lock it from rotating. The distal part 160 of the collet 158 may have facets with which the cap screw 166 can mate to turn the distal part 160 relative to the proximal part 162 to an extent necessary to release the wire 14.

The collets shown in these embodiments may include an internal counter-taper to optimise the land length over which the wire 14 is gripped. This advantageously limits the point loading on the wire 14 and possible consequent microstructural damage that could otherwise promote the formation of microstructural defects.

Figure 33:
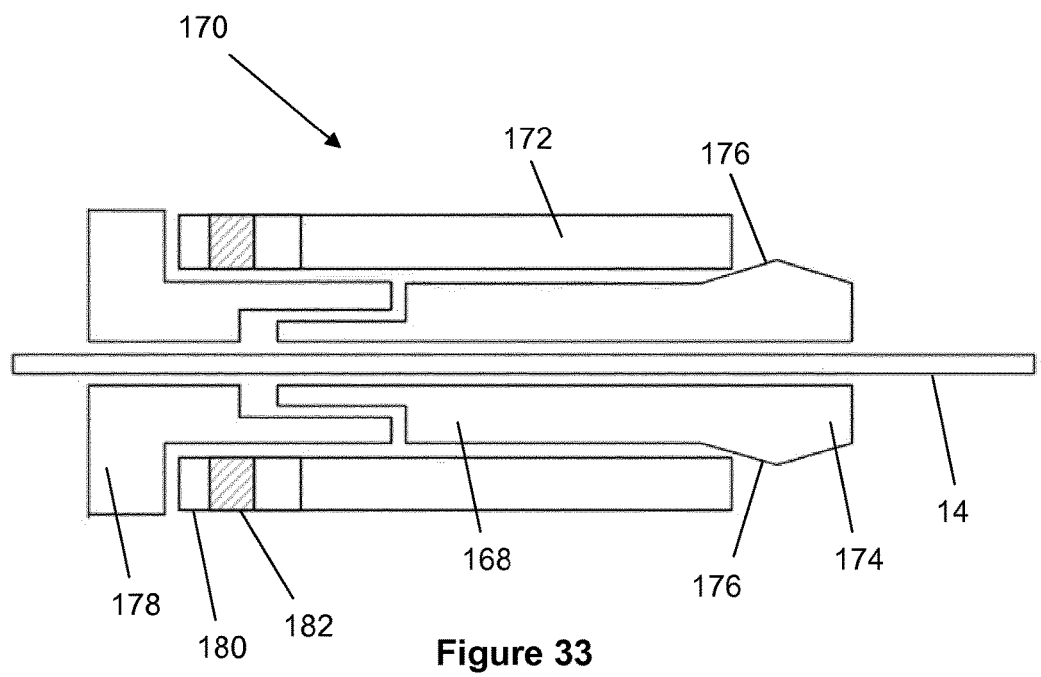
FIG. 33 is a schematic sectional side view of a further collet arrangement.

FIG. 33 shows an internal expanding collet 168 housed in a head of a transducer 170. In this embodiment, the collet 168 is integrated into the transducer 170 and so is integral to the device itself. A wire 14 extends through the full length of the collet 168 and protrudes distally and proximally from the transducer 170.

The transducer 170 shown in FIG. 33 has a tubular body 172 that surrounds the collet 168. The collet 168 has an enlarged distal head 174 that protrudes from the distal end of the body 172 and has a diameter greater than the internal diameter of the body 172. Inclined ramp surfaces 176 on a proximal side of the head 174 bear against the distal end of the body 172.

A torque screw 178 is disposed at the proximal end of the body 172. An annular backing nut 180 and a piezo stack 182 are sandwiched between the torque screw 178 and the body 172.

The collet 168 has a threaded proximal part in threaded engagement with the torque screw 178. The torque screw 178 therefore couples the collet 168 and hence the wire 14 to the transducer 170 to transmit ultrasonic energy from the transducer 170 into the wire 14. Moreover, turning the torque screw 178 draws the collet 168 proximally into the body of the transducer 170. As the collet 168 moves proximally relative to the body 172, the inclined ramp surfaces 176 of the enlarged distal head 174 bear against the distal end of the body 172 and cause the collet 168 to clamp radially onto the wire 14.

Figure 34A:
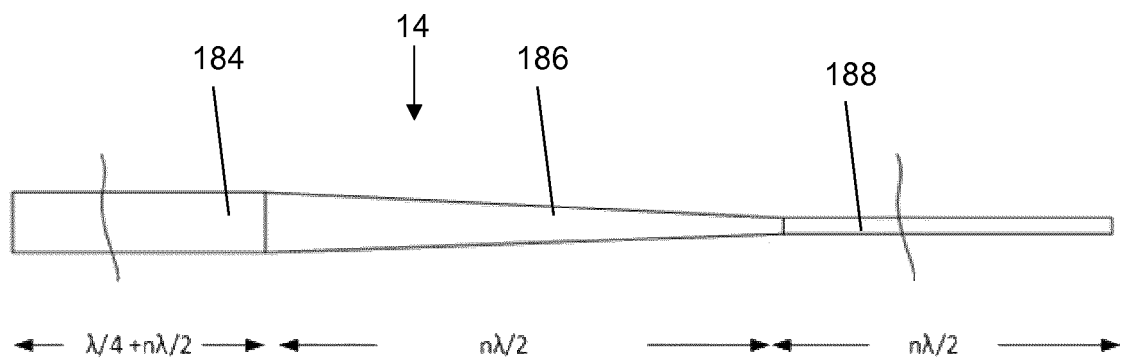
FIGS. 34a and 34b are schematic side views of a further active wire of the invention.
Figure 34B:
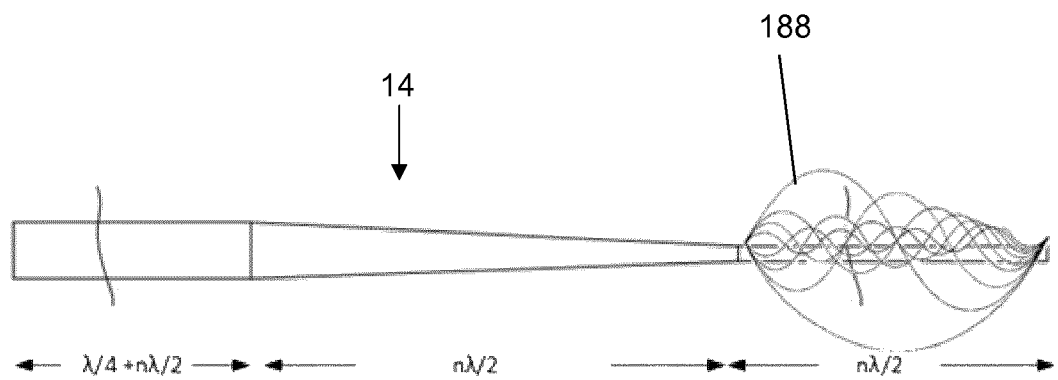

FIGS. 34*a* and 34*b* show a wire 14 that has a substantially straight proximal section 184, a distally-tapering intermediate section 186 and a substantially straight distal excavating section 188 for crossing a lesion. By virtue of the taper of the intermediate section 186 between them, the distal section 188 has a smaller diameter than the proximal section 184.

For example, the proximal section 184 may have a diameter of 0.43 mm and the distal section 188 may have a diameter of 0.25 mm. As the intermediate section 186 may extend over a metre in length, the taper between the proximal and distal sections 184, 188 is very slight and so is greatly exaggerated in these drawings.

The overall geometry of the wire including its nominal diameter and length are determined by the characteristic speed of sound in the material of the wire. This characteristic is determined for the materials chosen for the transducer and the wire. The dimensions of the straight and tapered sections of the wire are machined at functional intervals of wavelength.

Where nitinol materials are chosen, $\lambda$, $\lambda/2$ and $\lambda/4$ are determined to be 168 mm, 84 mm and 42 mm in this example. The chosen frequency will produce harmonics along the length of the wire and the loading of the tip of the wire will assist in establishing standing waves for non-characteristic lesions.

The distal section 188 can be tapered or can be uniform in diameter along its length and the harmonics can be $\lambda$ or at least $\lambda/4$. The system can produce harmonics over a range.

As the goal of the activated wire 14 is to excavate a lesion, dimensions are optimised with the purpose of excavating as great a volume as possible at a given waveform. In this respect, FIG. 34*b* shows that the distal section 188 of the wire 14, once activated, moves in a primary longitudinal mode, moving in and out, and also in a radial direction which maps out and excavates a greater volume at the distal end through the longitudinal movement of the wire 14. The distal section 188 of the wire 14 is also seen to move in other modes through lateral and undulating movements under the resonant wave and secondary modes of differential harmonics, dependent on the activating frequency and also the length of the distal section 188.

Figure 35:
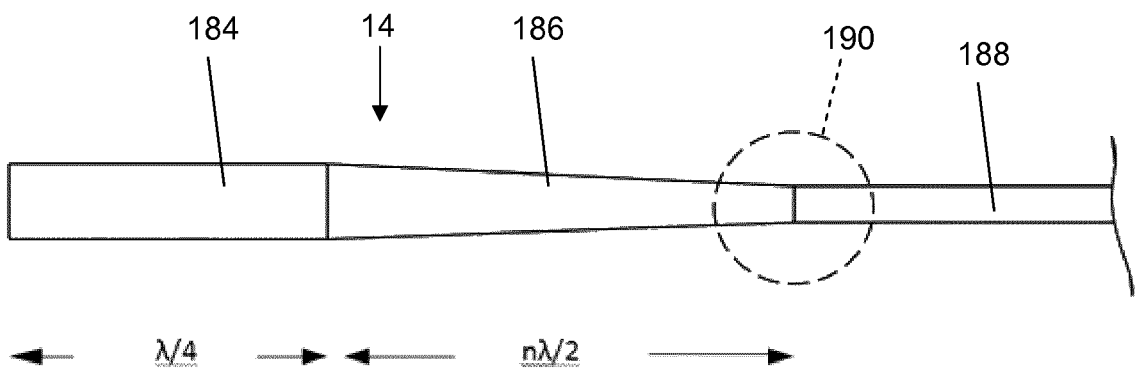
FIG. 35 is a schematic side view of an active wire of the invention.

FIG. 35 exemplifies how a wire 14 may be fabricated from sections welded together end-to-end. In this embodiment, the proximal section 184 is machined as a standard diameter to provide for amplification as well as to provide a standard connection for a proximally-loaded activation device. The proximal section 184 serves as a shaft that can be welded at a join 190, circled in FIG. 35, to one of a selection of different-diameter wires that may have custom distal ends and tips. This beneficially reduces the requirement to hold stock of various wire diameters as sections of a few different wire diameters may be assembled to produce wires of many required configurations. As the welded join 190 of the wire 14 is at a location of low stress, the loads applied to the join 190 in the course of activation will not lead to catastrophic fatigue failure.

Figure 36:
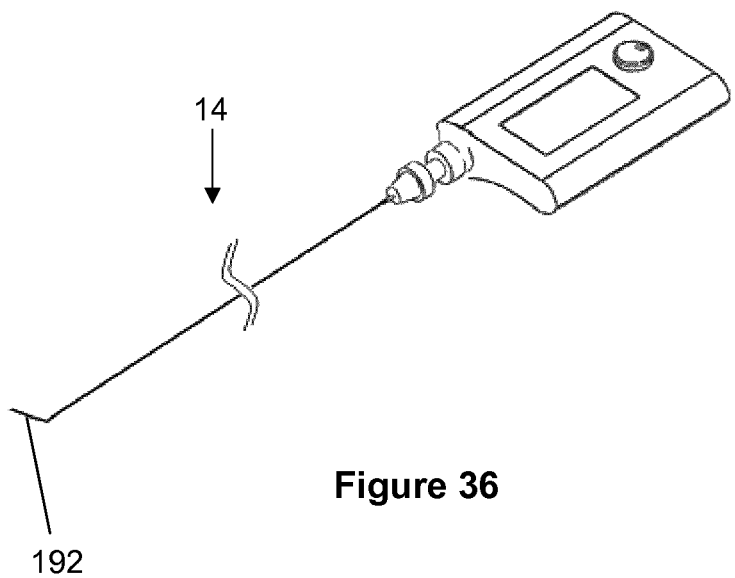
FIG. 36 is a perspective view of a variant of the invention in which the active wire has an angularly-offset distal end portion.
Figure 37:
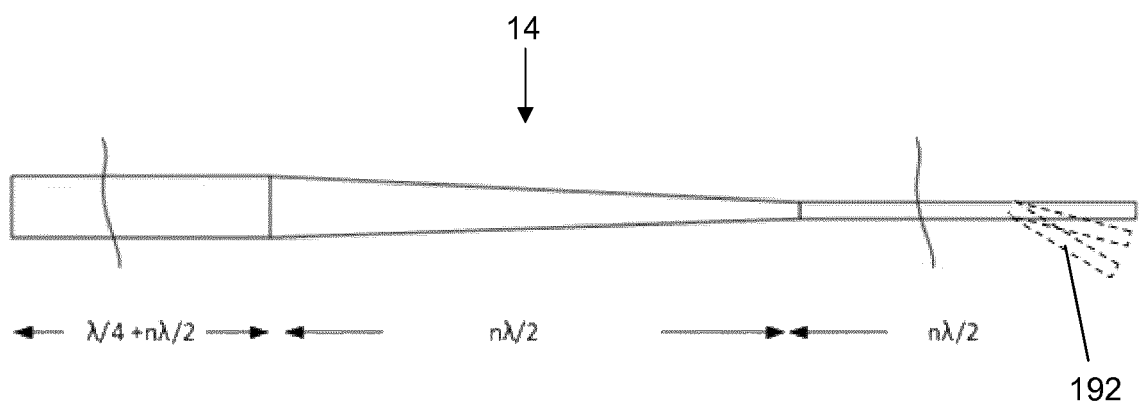
FIG. 37 is a schematic side view of an active wire having an angularly-offset distal end portion like that shown in FIG. 35.

Moving on to FIGS. 36 and 37, these drawings show a wire 14 that is formed or shaped to have an angularly-offset distal excavating section for crossing a lesion. In this embodiment, the distal section is not straight but is angled by virtue of a heat-set shaped tip 192. The dimensions of the tip 192 are optimised to provide improved performance in terms of steering to a lesion and excavation of the lesion. In particular, the angle of the tip 192 relative to the longitudinal axis of the distal section and the length of the tip 192 determine the ability of the wire 14 to turn into a specific side-branch artery. The angle and the length of the tip 192 also affect the manner in which the wire 14, once activated, will excavate a section of stenosed material.

If the dimensions of the tip 192 are characteristic of a harmonic, e.g. $\lambda/8$ or about. 22 mm in length, the wire 14 will open out a significantly larger tunnel in a lesion than say a 25 mm tip section. The amplitude of the waveform and the number of times the distal section of the wire 14 is passed through a calcific section will determine the diameter of the tunnel that is excavated.

If the angle of the tip 192 is too great, it will create a larger lever arm and so could fatigue the wire 14 excessively; conversely if the angle of the tip 192 is too small, then the wire 14 may not be steerable effectively. In this respect, FIG. 37 shows that the tip 192 may be offset from the longitudinal axis of the wire 14 by about 15° to 45°, allowing the tip 192 to disrupt and excavate a greater volume of a lesion. The tip 192 is suitably heat-treated, for example at over 500° C. for less than 10 minutes, in order to create a microstructure that is reliably resistant to crack propagation and hence to fatigue.

Figure 38A:
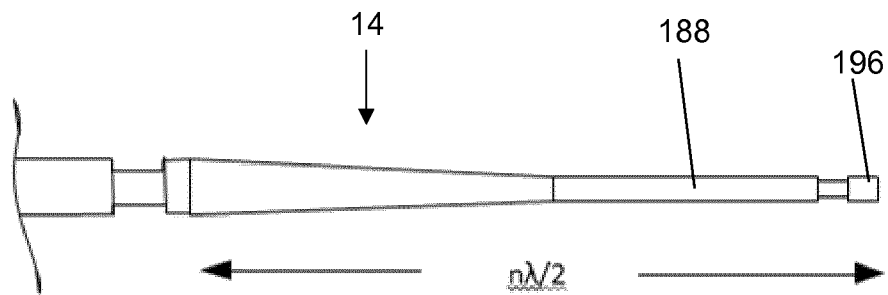
FIGS. 38a and 38b are schematic side views of a further active wire of the invention, including marker bands.
Figure 38B:
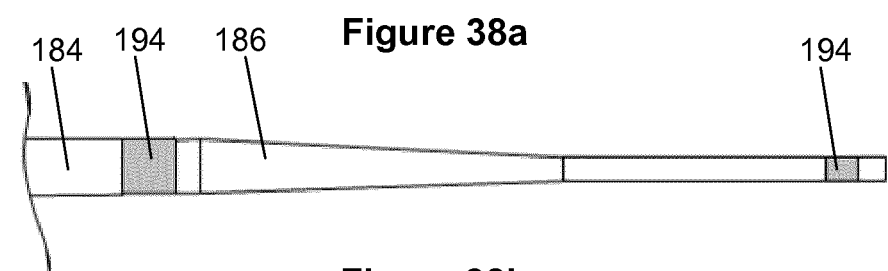

FIGS. 38*a* and 38*b* show how visibility of the location of the wire 14 in the patient's body may be enhanced by the use of marker bands 194, for example of gold. Such marker bands 194 may, for example, be fixed at locations close to (for example, about 3 mm from) the distal tip 196 of the wire 14 and also from the distal end of the proximal section 184, just before the start of the tapered intermediate section 186. The marker bands 194 are placed at locations of minimal load in use of the wire 14. This minimises the possibility that the marker bands 194 could become detached or that the wire 14 could fail at those locations. The marker bands 194 are apt to be flush-fitted into circumferential grooves that are ground around the wire 14.

Figure 39:
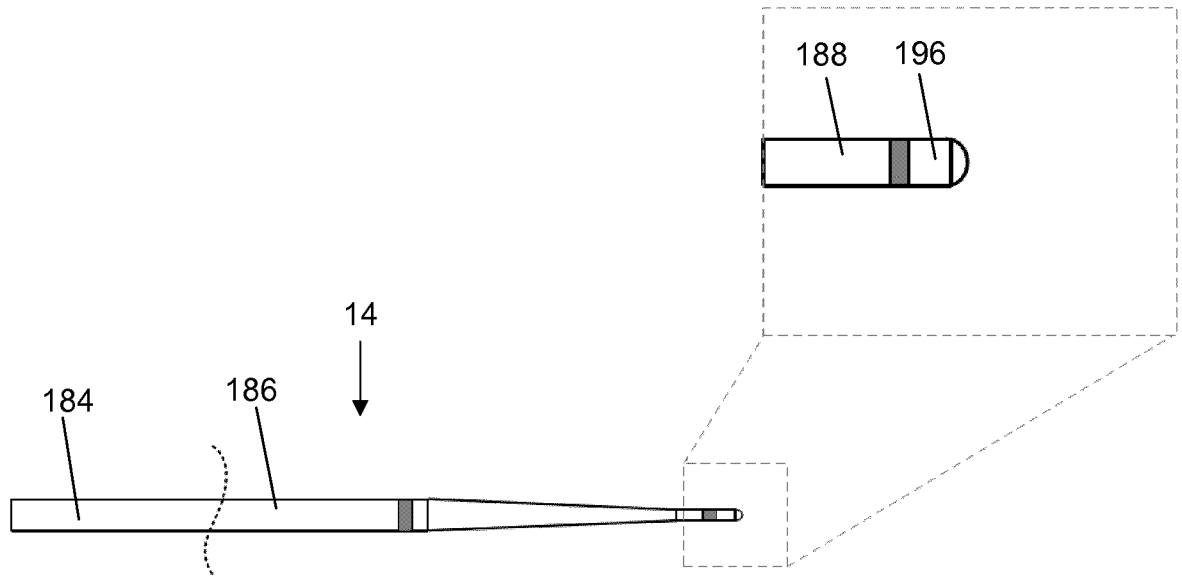
FIG. 39 is a schematic side view of another active wire of the invention.

FIG. 39 shows a variant in which the distal tip 196 of the wire 14 is rounded, with no sharp transitions. By way of example, in this instance the proximal section 184 may be 1800 mm long, the tapered intermediate section 186 may be 84 mm long and the distal section 188 may be 10 mm long. Again, marker bands 194 encircle the wire 14 close to the distal tip 196 of the wire 14 and the distal end of the proximal section 184.

Figure 40:
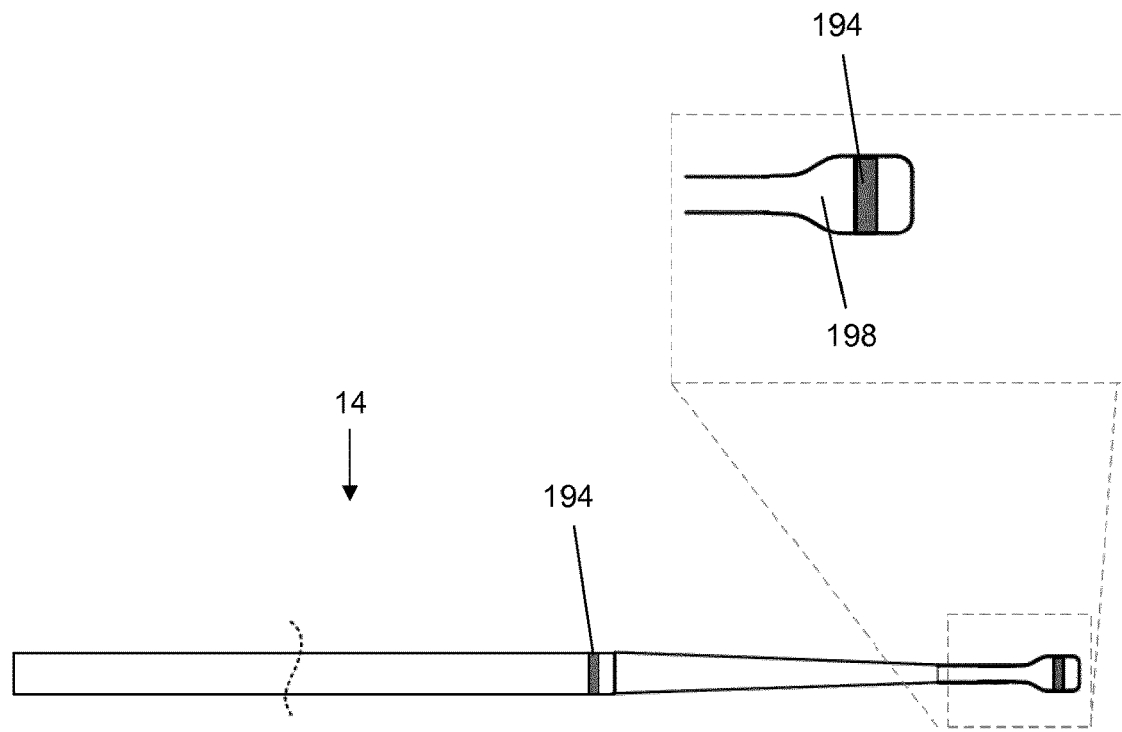
FIGS. 40 and 41 are schematic side views of other active wires of the invention, each having an enlarged, bulbous distal tip.
Figure 41:
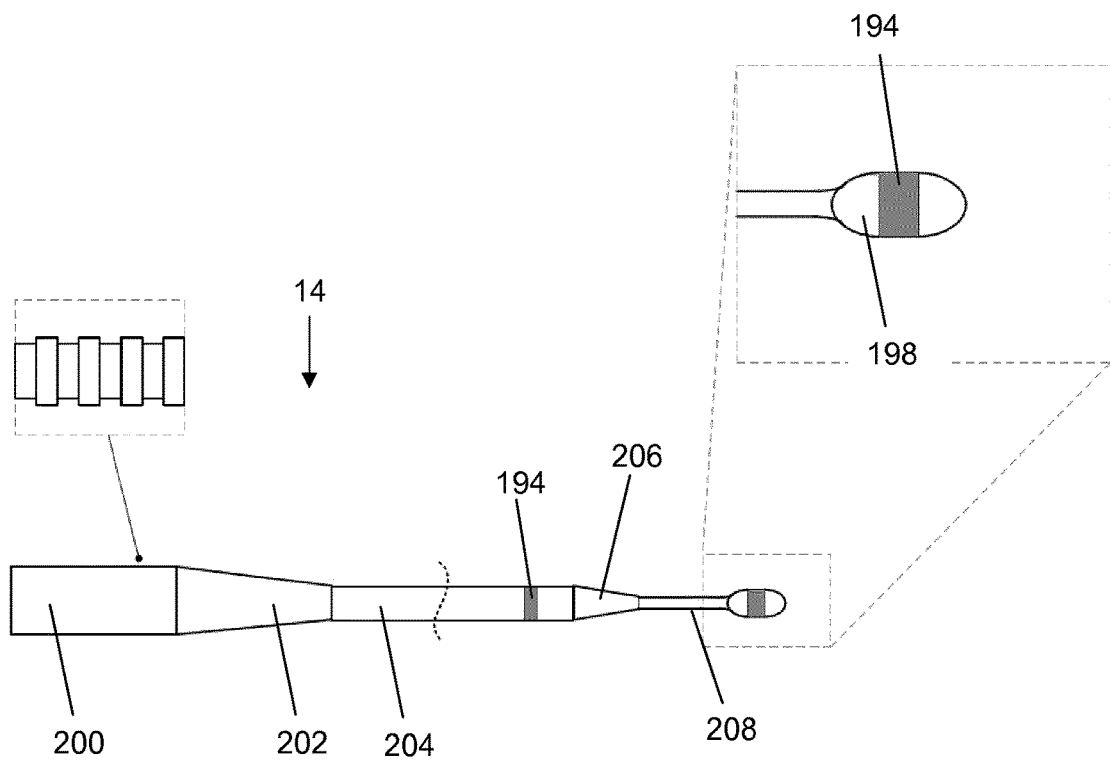

FIGS. 40 and 41 show other variants of the wire 14 that each have a bulbous distal tip 198, which is rounded to avoid sharp transitions. The bulbous tip 198 may, for example, be 3 mm to 4 mm in length and may have a diameter of just over 0.4 mm.

Apart from its bulbous tip 198, the wire shown in FIG. 40 is otherwise analogous to the wire 14 shown in FIG. 39.

Again, the wires 14 shown in FIGS. 40 and 41 have circumferential marker bands 194 that may be flush-fitted into circumferential grooves ground around the wire 14. Conveniently, as shown, the bulbous tip 198 may be encircled by one of the marker band 194.

In the example shown in FIG. 41, the wire has a proximal portion that comprises a straight section 200 and a distally-tapering section 202. The straight section 200 may have a textured surface as shown, to improve engagement with an activation device.

The proximal portion is welded to an intermediate portion that constitutes most of the length of the wire 14. The intermediate portion also comprises a straight section 204 and a short distally-tapering section 206. A marker band 194 is shown encircling the straight section 204 close to the distally-tapering section 206 of the intermediate portion 194. Finally, a short, narrow distal section 208 extends distally from the intermediate portion 186 to the bulbous tip 198.

Turning finally to FIGS. 42*a* to 42*c*, these schematic views illustrate how the wire 14 can be used initially as an active wire to cross a lesion 210 and then as a guide wire to transport a follow-on diagnostic or therapeutic device 214 to the lesion 210.

In FIG. 42*a*, the wire 14 is shown extending distally through an introducer sheath 135 and into the patient's body 137. The distal tip of the wire 14 has been navigated through the patient's vasculature 212 to reach the lesion 210. The wire 14 is shown here activated by an activation unit 2 and hence excavating and crossing the lesion 210 by virtue of vibration of the distal tip.

In this example, the activation unit 2 is shown at the proximal end of the wire 14. However, the activation unit 2 could instead be positioned at any of a plurality of intermediate positions along the proximal portion of the wire 14 that protrudes from the patient's body 137.

Once the lesion 210 has been successfully crossed as shown in FIG. 42b, the wire 14 is deactivated and left in situ within the patient's vasculature 212. The activation unit 2 is then removed from the wire 14, exposing the proximal end of the wire 14.

The deactivated wire 14 can now serve as a guide wire to transport the follow-on diagnostic or therapeutic device 214 to the lesion 210 as shown in FIG. 42c. The device 214 may most conveniently be threaded onto the proximal end of the wire 14. However, in principle, the device 214 could instead be attached to the wire 14 at any location along the proximal portion of the wire 14 that remains outside the patient's body 137.

EXAMPLE EMBODIMENTS OF THE DISCLOSURE

The following numbered clauses define certain example embodiments of the present disclosure.

Clause 1.

Endovascular apparatus for crossing through an obstruction in a blood vessel, the apparatus comprising: an elongate endovascular wire; and a coupling for, in use, transmitting ultrasonic energy along the wire from a source of the ultrasonic energy to an active tip at a distal end of the wire; wherein the coupling is arranged to couple the source to the wire at any of a plurality of discrete operational positions along the length of the wire for said transmission of ultrasonic energy to the active tip.

Clause 2.

The apparatus of Clause 1, wherein the coupling is arranged to enable relative longitudinal movement between the source and the wire when moving between the operational positions.

Clause 3.

The apparatus of Clause 2, wherein the coupling is arranged to enable said relative longitudinal movement while remaining attached to the wire.

Clause 4.

The apparatus of Clause 2, wherein the coupling is arranged to enable said relative longitudinal movement by being removed from and reattached to the wire.

Clause 5.

The apparatus of Clause 4, wherein the coupling and/or the source comprises distal and proximal or lateral openings for longitudinal insertion and withdrawal of the wire.

Clause 6.

The apparatus of Clause 4, wherein the coupling and/or the source comprises at least one longitudinal slot for entry or exit of the wire in a lateral direction transverse to a longitudinal axis of the wire.

Clause 7.

The apparatus of Clause 6, further comprising a locking mechanism that is arranged to capture the wire after lateral entry of the wire through the slot and to release the wire for lateral exit of the wire through the slot.

Clause 8.

The apparatus of Clause 7, wherein the locking mechanism comprises at least one locking member that is rotatable about the wire to capture and to release the wire.

Clause 9.

The apparatus of any preceding Clause, wherein the coupling is arranged to clamp the wire when at any of the operational positions.

Clause 10.

The apparatus of Clause 9, wherein the coupling comprises a collet that is compressible radially onto the wire in response to longitudinal movement or longitudinal compression of the collet.

Clause 11.

The apparatus of Clause 10, wherein the collet comprises at least one mating face that is engaged with the source, that face being inclined relative to a longitudinal axis of the collet.

Clause 12.

The apparatus of Clause 11, wherein the mating face is defined by a tapered end of the collet.

Clause 13.

The apparatus of Clause 11 or Clause 12, wherein the collet is movable longitudinally within or relative to a transducer that serves as the source.

Clause 14.

The apparatus of Clause 13, comprising a screw thread between the collet and the transducer, which screw thread is arranged to move the collet longitudinally and to couple the collet to the transducer.

Clause 15.

The apparatus of any preceding Clause, wherein the wire extends through the source and has portions that extend, respectively, proximally and distally from the source.

Clause 16.

The apparatus of Clause 15, wherein the proximally-extending portion of the wire exits a proximal end of the source.

Clause 17.

The apparatus of Clause 15, wherein the proximally-extending portion of the wire exits the source on an axis transverse to a longitudinal axis of the distally-extending portion of the wire.

Clause 18.

The apparatus of any preceding Clause, wherein the operational positions are marked on the wire.

Clause 19.

The apparatus of any preceding Clause, wherein the operational positions are characteristic of harmonics of the wire at an activation frequency of the source.

Clause 20.

Endovascular apparatus for crossing through an obstruction in a blood vessel, the apparatus comprising:
 an electrically-driven source of ultrasonic energy;
 a coupling for exciting an endovascular wire, in use, to transmit ultrasonic energy along the wire from the source thereby coupled to the wire to an active tip at a distal end of the wire; and
 a signal acquisition and processing system that is configured to capture and respond to operational parameters of the apparatus as the active tip approaches or crosses through an obstruction in use.

Clause 21.

The apparatus of Clause 20, wherein the signal acquisition and processing system is configured to monitor variations of frequency and/or amplitude of current drawn by, or voltage dropped across, the source of ultrasonic energy.

Clause 22.

The apparatus of Clause 20 or Clause 21, wherein the signal acquisition and processing system is configured to modulate excitation voltage applied to, or excitation current supplied to, the source of ultrasonic energy.

Clause 23.

The apparatus of Clause 22, wherein the signal acquisition and processing system is configured to control the source of ultrasonic energy by varying frequency and/or amplitude of the excitation voltage applied to the source of ultrasonic energy.

Clause 24.

The apparatus of Clause 23, wherein the signal acquisition and processing system is configured to drive the frequency of the excitation voltage by employing a phase difference between the excitation voltage and the excitation current in conjunction with amplitude of the excitation voltage.

Clause 25.

The apparatus of any of Clauses 20 to 24, wherein the signal acquisition and processing system is configured to monitor variations in frequency or amplitude of vibration of the wire via the coupling. 26. The apparatus of Clause 25, wherein the signal acquisition and processing system comprises an amplitude feedback controller and is configured to use a resonant frequency as an operating point of control.

Clause 27.

The apparatus of Clause 25 or Clause 26, wherein the signal acquisition and processing system is configured to infer displacement of the active tip of the wire from waveforms in the wire determined from said variations in frequency of vibration of the wire.

Clause 28.

The apparatus of Clause 27, wherein the signal acquisition and processing system is configured to employ numerical algorithms selected for specific types of the wire.

Clause 29.

The apparatus of Clause 27 or Clause 28, wherein the signal acquisition and processing system is configured to estimate an area mapped out by said displacement of the active tip of the wire in open and occluded vasculature for gelatinous, fibrous and calcified lesions.

Clause 30.

The apparatus of any of Clauses 20 to 29, wherein the signal acquisition and processing system is configured to monitor approach to an obstruction and/or to determine characteristics of an obstruction from the captured operational parameters.

Clause 31.

The apparatus of any of Clauses 20 to 30, wherein the signal acquisition and processing system is configured to compare relative contributions of losses from anatomical tortuosity in navigating the active tip to the obstruction versus losses arising from the passage of the active tip through the obstruction.

Clause 32.

The apparatus of Clause 31, wherein the signal acquisition and processing system is configured to pulse or vary a drive signal to the source of ultrasonic energy.

Clause 33.

The apparatus of any of Clauses 20 to 32, wherein the signal acquisition and processing system is configured to run an algorithm specific to the endovascular wire type to estimate deflection of the active tip, when excited, and to estimate a tunnel diameter extending through the obstruction.

Clause 34.

The apparatus of any of Clauses 20 to 33, wherein the signal acquisition and processing system is configured:
to monitor modulation of transmitted signals and to control voltage applied to the source of ultrasonic energy automatically to compensate for background energy loss encountered in the wire as the active tip approaches the obstruction; and
to distinguish the background energy loss from additional energy loss as the active tip passes through the obstruction and to compensate for the background energy loss to sustain displacement at the active tip.

Clause 35.

The apparatus of any of Clauses 20 to 34, further comprising a manual override that is operable to modulate power output of the source of ultrasonic energy.

Clause 36.

The apparatus of any of Clauses 20 to 35, wherein the signal acquisition and processing system is configured to compare the captured operational parameters with stored data that characterises known obstructions, and to characterise the obstruction with reference to that comparison.

Clause 37.

The apparatus of any of Clauses 20 to 36, wherein the signal acquisition and processing system further comprises an output to a user interface and/or to an external data acquisition system.

Clause 38.

The apparatus of any of Clauses 20 to 37, wherein the signal acquisition and processing system further comprises an input from a user interface and/or from an external data network.

Clause 39.

The apparatus of any of Clauses 20 to 38, wherein the signal acquisition and processing system is configured to modify or change a control algorithm in response to variation in the operational parameters of the apparatus arising from interaction of the active tip with an obstruction in use.

Clause 40.

The apparatus of any of Clauses 20 to 39, wherein the signal acquisition and processing system is configured to output data to an external data network and to receive data from the network in response and, on receiving data from the network, to modify or change a control algorithm accordingly.

Clause 41.

The apparatus of Clause 40, wherein the signal acquisition and processing system is configured to output data to the network representing variation in the operational parameters of the apparatus arising from interaction of the active tip with an obstruction in use.

Clause 42.

The apparatus of any preceding Clause, wherein the source comprises a transducer vibrating at a frequency of between 20 kHz and 60 kHz.

Clause 43.

The apparatus of Clause 42, wherein the transducer vibrates at a frequency of between 35 kHz and 45 kHz.

Clause 44.

The apparatus of Clause 43, wherein the transducer vibrates at a frequency of between 37 kHz and 43 kHz. 45. The apparatus of Clause 44, wherein the transducer vibrates at a frequency substantially equal to 40 KHz.

Clause 46.

The apparatus of any preceding Clause, further comprising a follow-on endovascular diagnostic or therapeutic device that is transportable distally along the wire into a patient's vasculature after uncoupling the source from the wire.

Clause 47.

A communication system comprising the apparatus of any preceding Clause in data communication with a computer system that is arranged to receive data from the apparatus, to optimise and update control algorithms accordingly and to output the optimised, updated control algorithms to the apparatus.

Clause 48.

The communication system of Clause 47, wherein two or more such apparatuses are in data communication with the computer system, which is arranged to optimise control algorithms in accordance with data received from multiple procedures performed using the apparatuses and to output the optimised, updated control algorithms to the apparatuses.

Clause 49.

An elongate endovascular wire for crossing through an obstruction in a blood vessel, the wire comprising a coupling for, in use, transmitting ultrasonic energy along the wire from a source of the ultrasonic energy to an active tip at a distal end of the wire, wherein the coupling is arranged to couple the source to the wire at any of a plurality of discrete operational positions along the length of the wire for said transmission of ultrasonic energy to the active tip.

Clause 50.

An elongate endovascular wire for crossing through an obstruction in a blood vessel, the wire comprising:
 a coupling for, in use, transmitting ultrasonic energy along the wire from a source of the ultrasonic energy to an active tip at a distal end of the wire; and
 a cutting device on the coupling or on the wire for cutting through or scoring the wire to sever the coupling from a portion of the wire extending distally from the cutting device.

Clause 51.

The wire of Clause 50, wherein the cutting device comprises at least one blade that is movable transversely relative to a longitudinal axis of the wire.

Clause 52.

An elongate endovascular wire for crossing through an obstruction in a blood vessel, the wire comprising:
 a coupling for, in use, transmitting ultrasonic energy along the wire from a source of the ultrasonic energy to an active tip at a distal end of the wire;
 wherein the coupling comprises: a screw connector that is fixed to a proximal end of the wire; and a rotary sleeve that, in a first longitudinal position, is engaged with the screw connector to turn the screw connector into engagement with the source of the ultrasonic energy and that is then movable into a second longitudinal position to decouple the sleeve from the screw connector and the wire.

Clause 53.

The wire of Clause 52, wherein the first longitudinal position is disposed proximally with respect to the second longitudinal position.

Clause 54.

An elongate endovascular wire for crossing through an obstruction in a blood vessel, the wire comprising a proximal section; a distal tip section of smaller diameter than the proximal section; and a distally-tapering intermediate section extending between the proximal and distal tip sections, wherein the wire is unsleeved over substantially its entire length.

Clause 55.

The wire of Clause 54, comprising at least one welded join between at least two of said sections.

Clause 56.

The wire of Clause 54 or Clause 55, wherein the distal tip section comprises a bulbous distal extremity.

Clause 57.

The wire of any of Clauses 54 to 56, wherein the distal tip section comprises a distal portion that is offset angularly with respect to a longitudinal axis of the wire.

Clause 58.

The wire of any of Clauses 54 to 57, wherein a marker band encircles at least the distal tip section.

Clause 59.

The wire of any of Clauses 54 to 58, having an overall length of between 500 mm and 2500 mm.

Clause 60.

The wire of any of Clauses 54 to 59, wherein the proximal section is of uniform diameter along its length.

Clause 61.

The wire of Clause 60, wherein the diameter of the proximal section is from 0.014" to 0.035" (about 0.36 mm to about 0.89 mm).

Clause 62.

The wire of any of Clauses 54 to 61, wherein the proximal section of the wire has a length of from 500 mm to 2000 mm.

Clause 63.

The wire of any of Clauses 54 to 62, wherein the length of each of said sections is a function or multiple of 1/4, where 1 is a driving frequency that results in resonance in the wire.

Clause 64.

The wire of any of Clauses 54 to 63, wherein the distal section is tapered or of a constant diameter along its length.

Clause 65.

The wire of Clause 64, wherein the distal section has a diameter of from 0.003" to 0.014" (about 0.08 mm to about 0.36 mm).

Clause 66.

Endovascular apparatus comprising the wire of any of Clauses 49 to 65 and a source of ultrasonic energy coupled to the wire.

Clause 67.

An activation unit for conveying ultrasonic energy into an elongate endovascular wire, the unit comprising:
 a source of the ultrasonic energy; and
 a coupling that is arranged to couple the source to the wire at any of a plurality of discrete operational positions along the length of the wire.

Clause 68. The unit of Clause 67, wherein the coupling is arranged to enable relative longitudinal movement between the source and the wire when moving between the operational positions.

Clause 69.

The unit of Clause 68, wherein the coupling is arranged to enable said relative longitudinal movement while remaining attached to the wire.

Clause 70.

The unit of Clause 68, wherein the coupling is arranged to enable said relative longitudinal movement by being removed from and reattached to the wire.

Clause 71.

The unit of any of Clauses 67 to 70, wherein the source comprises a transducer vibrating at a frequency of between 20 kHz and 60 kHz.

Clause 72.

The unit of Clause 71, wherein transducer vibrates at a frequency of between 35 kHz and 45 kHz.

Clause 73.

The unit of Clause 72, wherein transducer vibrates at a frequency of between 37 kHz and 43 kHz.

Clause 74.

The unit of Clause 73, wherein transducer vibrates at a frequency of between or substantially equal to 40 KHz.

Clause 75. The unit of any of Clauses 67 to 74, further comprising a visual, haptic and/or audio user interface.

Clause 76.

A method of mitigating an obstruction in a passageway, the method comprising:
  coupling a source of ultrasonic energy to an elongate wire at any of a plurality of discrete operational positions along the length of the wire; and
  transmitting ultrasonic vibrations from the source along the wire to vibrate an active tip at a distal end of the wire in contact with the obstruction.

Clause 77.

The method of Clause 76, comprising effecting relative longitudinal movement between the source and the wire when moving between the operational positions.

Clause 78.

The method of Clause 77, comprising effecting said relative longitudinal movement while the source remains attached to the wire.

Clause 79.

The method of Clause 78, comprising moving the wire longitudinally while holding the source substantially stationary.

Clause 80.

The method of Clause 77, comprising effecting said relative longitudinal movement by removing the source from the wire and reattaching the source to the wire at a different longitudinal position.

Clause 81.

The method of Clause 80, comprising moving the source longitudinally while holding the wire substantially stationary.

Clause 82.

The method of Clause 80 or Clause 81, comprising removing the source from the wire or attaching the source to the wire by relative movement between the source and the wire in a lateral direction transverse to a longitudinal axis of the wire.

Clause 83.

The method of any of Clauses 76 to 82, comprising clamping the wire when the source is at any of the operational positions.

Clause 84.

A method of mitigating an obstruction in a passageway, the method comprising:
  transmitting ultrasonic vibrations from a source of ultrasonic energy along an elongate wire to vibrate an active tip at a distal end of the wire in contact with the obstruction; and
  delivering a follow-on diagnostic or therapeutic device distally along the wire.

Clause 85.

The method of Clause 84, comprising removing the source from the wire before delivering the follow-on device along the wire.

Clause 86.

A method of mitigating an obstruction in a passageway, the method comprising:
  transmitting ultrasonic vibrations along a wire from an electrically-driven source coupled with the wire to vibrate an active tip at a distal end of the wire in contact with the obstruction; and
  sensing the response of the vibrating wire to interaction with the obstruction as the active tip encounters and crosses through the obstruction.

Clause 87.

The method of Clause 86, further comprising comparing sensed data representing the response of the vibrating wire with stored data representing the response of a corresponding vibrating wire to interaction with a known obstruction.

Clause 88.

The method of Clause 86 or Clause 87, further comprising, in response to sensing the response of the vibrating wire, adjusting amplitude or frequency of the ultrasonic vibrations transmitted to the active tip along the wire.

Clause 89.

The method of any of Clauses 86 to 88, comprising sensing amplitude of vibration of the wire and controlling the source to maintain a resonant frequency in the wire.

Clause 90.

The method of any of Clauses 86 to 89, comprising modifying or changing a control algorithm in response to variation in the response of the vibrating wire. 91. The method of any of Clauses 86 to 90, comprising: outputting data to an external data network; receiving data from the network in response; and, on receiving data from the network, modifying or changing a control algorithm accordingly.

Clause 92.

The method of Clause 91, comprising: outputting data to the network representing variation in the response of the vibrating wire.

Clause 93.

The method of any of Clauses 86 to 92, comprising: outputting data to an external computer system; in the external computer system, optimising and updating a control algorithm in accordance with that data; outputting the optimised, updated control algorithm from the external computer system; and using the optimised, updated control algorithm to control vibration of the wire.

Clause 94.

The method of Clause 93, wherein the computer system optimises the control algorithm in accordance with data received from multiple procedures.

Clause 95.

A method of characterising an obstruction in a blood vessel, the method comprising comparing measured data, representing the response of a pre-delivered vibrating endovascular wire to interaction with the obstruction, with stored data representing the response of a corresponding vibrating endovascular wire to interaction with a known obstruction.

Clause 96.

The method of Clause 95, comprising adjusting vibration of the pre-delivered endovascular wire in response to the comparison between the measured data and the stored data.

Clause 97.

The method of Clause 95 or Clause 96, comprising the preliminary steps of selecting an endovascular wire of a particular type and selecting an algorithm specific to that type of endovascular wire for use in determining the response of the selected wire to an obstruction.

The invention claimed is:

1. An activation unit for conveying ultrasonic energy into an elongate endovascular wire, the activation unit comprising:

a handheld housing:
a source of the ultrasonic energy disposed within the housing, the source comprising an ultrasonic transducer; and
a coupling configured to couple the source to the wire by clamping the wire at any of a plurality of discrete operational positions along the length of the wire,
wherein the activation unit is configured to receive the wire such that the wire extends through the source and the coupling and such that a first portion of the wire extends distally from the housing and a second portion of the wire extends proximally from the housing, and
wherein the activation unit is configured to damp excitation of the second portion of the wire extending proximally from the housing.

2. The activation unit of claim 1, wherein the coupling is configured to enable the housing to be longitudinally translated between the operational positions.

3. The activation unit of claim 2, wherein the coupling is configured to enable the housing to be longitudinally translated between the operational positions while remaining attached to the wire.

4. The activation unit of claim 2, wherein the coupling is configured to enable the housing to be longitudinally translated between the operational positions by being removed from and reattached to the wire.

5. The activation unit of claim 1, wherein the activation unit comprises distal and proximal openings for longitudinal insertion and withdrawal of the wire.

6. The activation unit of claim 1, wherein the housing comprises user input controls and a user interface.

7. The activation unit of claim 6, wherein the user interface is configured to communicate performance of a device comprising the activation unit.

8. The activation unit of claim 7, wherein the user interface is configured to communicate performance of the device comprising the activation unit via audio, visual, or haptic means.

9. The activation unit of claim 1, wherein the coupling comprises a collet that is radially compressible onto the wire.

10. The activation unit of claim 9, wherein the collet comprises a mating face that is engaged with the source, the mating face being inclined relative to a longitudinal axis of the collet.

11. The activation unit of claim 10, wherein the mating face is defined by a tapered end of the collet.

12. The activation unit of claim 9, wherein the collet is moveable longitudinally within or relative to the ultrasonic transducer.

13. The activation unit of claim 12, further comprising a screw thread disposed between the collet and the ultrasonic transducer and configured to enable the collet to move longitudinally relative to the wire and to couple the collet to the ultrasonic transducer.

14. The activation unit of claim 1, wherein the coupling is operable by a locking mechanism on the housing.

15. An endovascular apparatus for penetrating an occlusion in a blood vessel, the endovascular apparatus comprising:
an elongate endovascular wire; and
an activation unit for conveying ultrasonic energy into the wire, the activation unit comprising:
a handheld housing;
a source of the ultrasonic energy, the source comprising an ultrasonic transducer disposed within the housing; and
a coupling configured to couple the source to the wire by clamping the wire at any of a plurality of discrete operational positions along the length of the wire,
wherein the activation unit is configured to receive the wire such that the wire extends through the source and the coupling and such that a first portion of the wire extends distally from the housing and a second portion of the wire extends proximally from the housing, and
wherein the activation unit is configured to damp excitation of the second portion of the wire extending proximally from the housing.

16. The endovascular apparatus of claim 15, wherein the second portion of the wire extending proximally from the housing exits and extends from a proximal end of the source.

17. The endovascular apparatus of claim 16, wherein the second portion of the wire extending proximally from the housing exits the source on an axis transverse to a longitudinal axis of the first portion of the wire extending distally from the housing.

18. The endovascular apparatus of claim 15, wherein the wire includes markings at intervals corresponding to the plurality of discrete operational positions.

19. The endovascular apparatus of claim 18, wherein the plurality of discrete operational positions are characteristic of harmonics of a predetermined activation frequency.

20. An endovascular apparatus for penetrating an occlusion in a blood vessel, the endovascular apparatus comprising:
an elongate endovascular wire having a plurality of discrete operational positions marked along the length of the wire, the plurality of discrete operational positions being characteristic of harmonics of a predetermined activation frequency;
a handheld housing;
an ultrasonic energy source included in the housing and comprising an ultrasonic transducer; and
a coupling configured to couple the ultrasonic energy source to the wire by locking to the wire at any of the plurality of discrete operational positions marked along the length of the wire,
wherein the housing, the source, and the coupling are configured such that the wire extends through the ultrasonic energy source and the coupling and such that a first portion of the wire extends distally from the housing and a second portion of the wire extends proximally from the housing.

21. The endovascular apparatus of claim 20, wherein the housing is further configured to damp excitation of the second portion of the wire.

22. The endovascular apparatus of claim 20, wherein the ultrasonic energy source further comprises an acoustic horn disposed between the ultrasonic transducer and the coupling.

23. The endovascular apparatus of claim 20, wherein the housing comprises a user interface configured to communicate performance of a device comprising the activation unit.

24. The endovascular apparatus of claim 23, further comprising a processor configured to process data obtained from measurements of an ultrasonic waveform generated by the activation unit and out the processed data for display by the user interface.

* * * * *